United States Patent
Suzuki et al.

(10) Patent No.: US 11,932,723 B2
(45) Date of Patent: Mar. 19, 2024

(54) HIGH-PURITY 3,4-EPOXYCYCLOHEXYLMETHYL METHACRYLATE

(71) Applicant: DAICEL CORPORATION, Osaka (JP)

(72) Inventors: Hirose Suzuki, Tokyo (JP); Yoshito Nakai, Tokyo (JP)

(73) Assignee: DAICEL CORPORATION, Osaka (JP)

(*) Notice: Subject to any disclaimer, the term of this patent is extended or adjusted under 35 U.S.C. 154(b) by 172 days.

(21) Appl. No.: 17/418,315

(22) PCT Filed: Dec. 24, 2019

(86) PCT No.: PCT/JP2019/050554
§ 371 (c)(1),
(2) Date: Jun. 25, 2021

(87) PCT Pub. No.: WO2020/138052
PCT Pub. Date: Jul. 2, 2020

(65) Prior Publication Data
US 2022/0089808 A1   Mar. 24, 2022

(30) Foreign Application Priority Data
Dec. 28, 2018   (JP) .................................. 2018-247154

(51) Int. Cl.
*C08G 59/24* (2006.01)
*C07D 303/16* (2006.01)
(Continued)

(52) U.S. Cl.
CPC ........... *C08G 59/24* (2013.01); *C07D 303/16* (2013.01); *C09D 163/00* (2013.01); *C09J 163/00* (2013.01)

(58) Field of Classification Search
CPC .... C08G 59/24; C07D 303/16; C09D 163/00; C09J 163/00
See application file for complete search history.

(56) References Cited

U.S. PATENT DOCUMENTS 5,426,193 A * 6/1995 Kuwana ............... C07D 303/16
549/546
8,278,388 B2   10/2012 Hongo et al.
(Continued)

FOREIGN PATENT DOCUMENTS

CN   108299343 A   7/2018
JP   2-262574 A   10/1990
(Continued)

OTHER PUBLICATIONS

International Search Report for International Application No. PCT/JP2019/050554, dated Mar. 3, 2020, with English translation.
(Continued)

*Primary Examiner* — Megan McCulley
(74) *Attorney, Agent, or Firm* — Birch, Stewart, Kolasch & Birch, LLP

(57) ABSTRACT

To provide 3,4-epoxycyclohexylmethyl methacrylate that is highly pure and that is useful as a raw material for functional materials or optical members having excellent transparency and heat resistance. An alicyclic epoxy compound product having a purity of 3,4-epoxycyclohexylmethyl methacrylate of 98.0 wt. % or greater and a total content of a compound represented by Formula (a) below and a compound represented by Formula (b) below of 1.3 wt. % or less. This alicyclic epoxy compound product preferably has a Hazen color number of 25 or less.

11 Claims, 1 Drawing Sheet

(51) Int. Cl.
     *C09D 163/00*     (2006.01)
     *C09J 163/00*     (2006.01)

(56) References Cited

U.S. PATENT DOCUMENTS

| | | |
|---|---|---|
| 8,975,349 B2 | 3/2015 | Funaki et al. |
| 2011/0015347 A1 | 1/2011 | Hongo et al. |
| 2012/0077946 A1 | 3/2012 | Funaki et al. |

FOREIGN PATENT DOCUMENTS

| | | |
|---|---|---|
| JP | 6-25203 A | 2/1994 |
| JP | 8-245511 A | 9/1996 |
| JP | 9-67308 A | 3/1997 |
| JP | 2000-154182 A | 6/2000 |
| WO | WO 2009/096374 A1 | 8/2009 |
| WO | WO 2010/140481 A1 | 12/2010 |
| WO | WO 2018/11027 A1 | 6/2018 |

OTHER PUBLICATIONS

Written Opinion of the International Searching Authority for International Application No. PCT/JP2019/050554, dated Jun. 16, 2021, with English translation.

\* cited by examiner

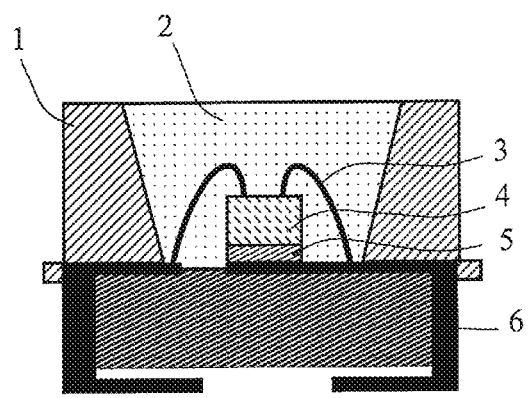

HIGH-PURITY 3,4-EPOXYCYCLOHEXYLMETHYL METHACRYLATE

TECHNICAL FIELD

The present invention relates to a high-purity 3,4-epoxycyclohexylmethyl methacrylate, a curable composition containing the same, and a cured product thereof, an encapsulant, an adhesive agent, a coating agent, and an optical member. The present application claims priority to JP 2018-247154 filed in Japan on Dec. 28, 2018, the content of which is incorporated herein.

BACKGROUND ART 3,4-Epoxycyclohexylmethyl methacrylate is a compound having two different types of curable groups, which are a cationically polymerizable epoxy group and a radically polymerizable methacryloyl group and can produce a cured product having various physical properties and characteristics by curing. The cured product obtained as described above can be used as, for example, a functional material or an optical member. That is, 3,4-epoxycyclohexylmethyl methacrylate can be used as a raw material for, for example, coating agents (including paints), encapsulants, adhesive agents, and optical materials. However, when 3,4-epoxycyclohexylmethyl methacrylate is produced, there are problems of raw materials and products readily being polymerized in a reaction or in solvent removal of a crude reaction solution. Furthermore, there are also problems of industrially produced 3,4-epoxycyclohexylmethyl methacrylate having a high degree of coloration and being likely to discolor over time.

Patent Document 1 describes that significant increase in polymerization suppression effect occurs when a combination of a particular polymerization preventing agent and a molecular oxygen-containing gas is used as polymerization inhibitors in reaction, removal of low-boiling fractions and/or formation of a product in the process of producing 3,4-epoxycyclohexylmethyl (meth)acrylate by epoxidizing cyclohexenylmethyl (meth)acrylate by using an oxidizing agent.

Patent Document 2 describes a method of producing 3,4-epoxycyclohexylmethyl (meth)acrylate by subjecting a crude reaction solution containing 3,4-epoxycyclohexylmethyl (meth)acrylate obtained by epoxidizing cyclohexenylmethyl (meth)acrylate by using an organic peracid, to treatment by (a) a process of water washing by using a device involving a short contact time, (b) a process of performing an alkali neutralization treatment, (c) a process of obtaining a liquid containing a low-boiling component content of 3 to 50 wt. % by removing low-boiling fractions at a heating temperature of 100° C. or lower under reduced pressure, and (d) a process of obtaining a liquid containing the low-boiling component content of less than 1 wt. % by removing low-boiling fractions at a heating temperature of 100° C. or lower under a reduced pressure that is ½ or less of that of the process (c). Note that, in Examples of Patent Document 1, the treatment for removal of low-boiling fractions of the (c) and (d) is performed by using a thin-film evaporator, and the condition of the first stage of the removal of low-boiling fractions is a heating temperature of 60° C. and a pressure of 150 mmHg, and the condition of the second stage of the removal of low-boiling fractions is a heating temperature of 60° C. and a pressure of 40 mmHg. According to this method, loss of valuable substances during the purification process can be reduced, a polymer content in the product can be reduced, and a product having a purity from 94 to 97% can be obtained.

Patent Document 3 describes a method of purifying 3,4-epoxycyclohexylmethyl (meth)acrylate, the method further including alkali solution washing in between the process (c) and the process (d) of the method in Patent Document 2 described above. In Examples of Patent Document 3, the treatment for removal of low-boiling fractions of the processes (c) and (d) is performed by using a flushing pipe. The vaporization conditions of the first stage and the second stage are the same as those in Patent Document 2. According to this method, coloration of the product can be prevented, and coloration over time of the product can be also effectively prevented.

Patent Document 4 describes that clogging of a pipe due to polymers can be suppressed by blowing molecular oxygen into a bottom hold tank of each thin-film evaporator in a process of continuous purification to perform solvent removal of a crude liquid that contains epoxidized cyclohexenylmethyl methacrylate and that is after the water washing by employing two or more thin-film evaporators that are linked.

CITATION LIST

Patent Document

Patent Document 1: JP H02-262574 A
Patent Document 2: JP H06-025203 A
Patent Document 3: JP H09-067308 A
Patent Document 4: JP H08-245511 A

SUMMARY OF INVENTION

Technical Problem

However, the 3,4-epoxycyclohexylmethyl methacrylate obtained by the method in the related art described above does not necessarily achieve satisfactory quality and characteristics for use as a raw material for, for example, recent high-performance materials and high-performance optical components. More specifically, a cured product obtained by curing the 3,4-epoxycyclohexylmethyl methacrylate produced by the method in the related art has poor transparency and heat resistance.

Therefore, an object of the present invention is to provide 3,4-epoxycyclohexylmethyl methacrylate that is highly pure and that is useful as a raw material for functional materials or optical members having excellent transparency and heat resistance.

Another object of the present invention is to provide 3,4-epoxycyclohexylmethyl methacrylate that is highly pure and that has excellent curability.

Yet another object of the present invention is to provide a curable composition that is useful as a raw material for functional materials or optical members having excellent transparency and heat resistance, a cured product thereof, an encapsulant, an adhesive agent, and a coating agent that contain the curable composition, and an optical member having a member formed from the cured product.

Note that, in the present specification, "product" is a term that means a form that is produced industrially and that can be commercially distributed and that does not mean a chemical substance itself. In the sense that a completely pure industrial product is not realistic, the "product" can be said to be a composition (containing a target substance as a main component and, for example, a composition containing almost 100 wt. %).

Solution to Problem

As a result of diligent research to achieve the objects described above, the inventors of the present invention found that, by subjecting a crude reaction solution containing 3,4-epoxycyclohexylmethyl methacrylate obtained by epoxidizing 3-cyclohexenylmethyl methacrylate to removal of low-boiling fractions by distillation and removal of high-boiling fractions by distillation, 3,4-epoxycyclohexylmethyl methacrylate that has a minimal content of particular impurities and that is highly pure and has excellent hue as well as excellent curability can be obtained, and a cured product having excellent transparency and heat resistance can be obtained by curing the 3,4-epoxycyclohexylmethyl methacrylate obtained as described above. The present invention has been completed by further studying based on these findings.

That is, an embodiment of the present invention provides an alicyclic epoxy compound product having a purity of 3,4-epoxycyclohexylmethyl methacrylate of 98.0 wt. % or greater and a total content of a compound represented by Formula (a) below and a compound represented by Formula (b) below of 1.3 wt. % or less.

[Chem. 1]

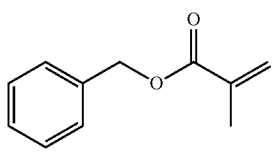
(a)

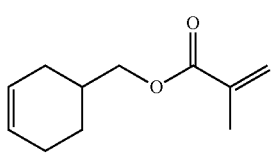
(b)

In the alicyclic epoxy compound product, the total content of the compound represented by Formula (a) above, the compound represented by Formula (b) above, and a compound represented by Formula (c) below is preferably 1.6 wt. % or less.

[Chem. 2]

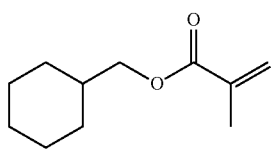
(c)

Furthermore, in the alicyclic epoxy compound product, the total content of the compound represented by Formula (a) above, the compound represented by Formula (b) above, the compound represented by Formula (c) above, and a compound represented by Formula (d) below is preferably 2.0 wt. % or less.

[Chem. 3]

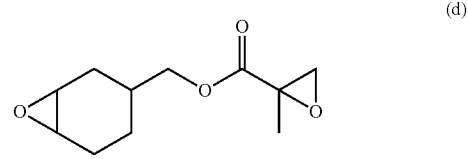
(d)

The Hazen color number of the alicyclic epoxy compound product is preferably 25 or less.

An embodiment of the present invention also provides a curable composition containing the alicyclic epoxy compound product described above.

The curable composition may further contain a curing agent and a curing accelerator.

The curable composition may further contain a curing catalyst.

An embodiment of the present invention also provides a cured product of the curable composition described above.

An embodiment of the present invention also provides an encapsulant containing the curable composition described above.

An embodiment of the present invention also provides an adhesive containing the curable composition described above.

An embodiment of the present invention also provides a coating agent containing the curable composition described above.

An embodiment of the present invention also provides an optical member having a member formed from the cured product described above.

Advantageous Effects of Invention

Because the alicyclic epoxy compound product according to an embodiment of the present invention contains high-purity 3,4-epoxycyclohexylmethyl methacrylate and has a low content of particular impurities, by curing a curable composition containing this alicyclic epoxy compound product, a cured product having excellent transparency and heat resistance can be obtained. Furthermore, the curable composition containing this alicyclic epoxy compound product exhibit faster curing speed than that of products in the related art.

According to the production method of an embodiment of the present invention, the alicyclic epoxy compound product having excellent characteristics described above can be efficiently, industrially produced.

Since the cured product and the optical member according to embodiments of the present invention are produced by curing the curable composition described above, the cured product and the optical member have excellent transparency and heat resistance.

Since the encapsulant, adhesive agent, and coating agent of embodiments of the present invention contain the curable composition having excellent characteristics as described above, a cured product having excellent physical properties such as transparency and heat resistance can be obtained in a relatively short time.

BRIEF DESCRIPTION OF DRAWINGS

FIG. 1 is a schematic view (cross-sectional view) of an optical member (optical semiconductor device) according to an embodiment of the present invention.

DESCRIPTION OF EMBODIMENTS

Alicyclic Epoxy Compound Product

An alicyclic epoxy compound product according to an embodiment of the present invention, that is, high-purity 3,4-epoxycyclohexylmethyl methacrylate, contains 3,4-epoxycyclohexylmethyl methacrylate (which is a compound represented by Formula (i) below)

[Chem. 4]

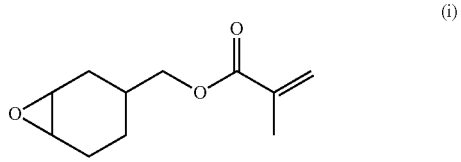

(i)

and the purity thereof (or content) is 98.0 wt. % or greater. The purity (or content) of the 3,4-epoxycyclohexylmethyl methacrylate is preferably 98.5 wt. % or greater, more preferably 99.0 wt. % or greater, and particularly preferably 99.5 wt. % or greater. By setting the purity of the 3,4-epoxycyclohexylmethyl methacrylate in the alicyclic epoxy compound product according to an embodiment of the present invention to be 98.0 wt. % or greater, curability of a curable composition containing the alicyclic epoxy compound product can be enhanced, and physical properties, especially heat resistance, of the cured product of the curable composition can be enhanced.

Furthermore, the alicyclic epoxy compound product according to an embodiment of the present invention has a total content of the compound represented by Formula (a) above and the compound represented by Formula (b) above of 1.3 wt. % or less. The total content of the compound represented by Formula (a) and the compound represented by Formula (b) is preferably 1.1 wt. % or less, more preferably 0.09 wt. % or less, and particularly preferably 0.07 wt. % or less. By setting the total content of the compound represented by Formula (a) and the compound represented by Formula (b) in the alicyclic epoxy compound product according to an embodiment of the present invention to 1.3 wt. % or less, physical properties, especially transparency and heat resistance, of a cured product of a curable composition containing the alicyclic epoxy compound product can be enhanced.

In the alicyclic epoxy compound product according to an embodiment of the present invention, the total content of the compound represented by Formula (a) above, the compound represented by Formula (b) above, and the compound represented by Formula (c) above is preferably 1.6 wt. % or less, more preferably 1.4 wt. % or less, even more preferably 1.0 wt. % or less, and particularly preferably 0.5 wt. % or less (e.g., 0.2 wt. % or less). By setting the total content of the compound represented by Formula (a), the compound represented by Formula (b), and the compound represented by Formula (c) to the range described above, physical properties, especially transparency and heat resistance, of the cured product of the curable composition containing the alicyclic epoxy compound product can be further enhanced.

In the alicyclic epoxy compound product according to an embodiment of the present invention, the total content of the compound represented by Formula (a) above, the compound represented by Formula (b) above, the compound represented by Formula (c) above, and the compound represented by Formula (d) above is preferably 2.0 wt. % or less, more preferably 1.5 wt. % or less, even more preferably 1.0 wt. % or less, and particularly preferably 0.5 wt. % or less (e.g., 0.2 wt. % or less). By setting the total content of the compound represented by Formula (a), the compound represented by Formula (b), the compound represented by Formula (c), and the compound represented by Formula (d) to the range described above, physical properties, especially transparency and heat resistance, of the cured product of the curable composition containing the alicyclic epoxy compound product can be further enhanced.

Note that the compound represented by Formula (b) (which is 3-cyclohexenylmethyl methacrylate) is a raw material of 3,4-epoxycyclohexylmethyl methacrylate and is a material in which an unreacted raw material is mixed in the alicyclic epoxy compound product. Furthermore, the compound represented by Formula (a) and the compound represented by Formula (c) are impurities contained in the raw material and are mixed in the alicyclic epoxy compound product. The compound represented by Formula (d) is an impurity generated as a byproduct mainly in the reaction (epoxidation) and can also be generated when the reaction product is subjected to vaporization or distillation (removal of solvents, removal of low-boiling fractions, removal of high-boiling fractions). The compound represented by Formula (d) is generated by further epoxidizing a double bond contained in the target compound represented by Formula (i).

The compound represented by Formula (a), the compound represented by Formula (b), and the compound represented by Formula (c) do not have cationically polymerizable groups, and the compound represented by Formula (d) does not have a radically polymerizable group. Therefore, when a large amount of these compounds are contained in the alicyclic epoxy compound product, the cured product obtained by curing the alicyclic epoxy compound product may not achieve desired physical properties (e.g., heat resistance and mechanical strength). Furthermore, because the compound represented by Formula (a) has an aromatic ring and the compound represented by Formula (b) has an unsaturated bond, the case where a large amount of these compounds is contained in the alicyclic epoxy compound product may cause deterioration of hue of the cured product.

Although the compound represented by Formula (a) and the compound represented by Formula (c) have lower boiling points than that of the target compound [compound represented by Formula (i)], the difference in the boiling points is not great, and thus the compound represented by Formula (a) and the compound represented by Formula (c) cannot be separated and removed by treatment for removal of low-boiling fractions (solvent removal treatment) by using an evaporator, such as a thin-film evaporator described in Patent Documents described above. Meanwhile, because the compound represented by Formula (d) has a boiling point that is higher than that of the target compound [compound represented by Formula (i)], the compound represented by Formula (d) cannot be separated and removed by treatment for removal of low-boiling fractions (solvent removal treatment) by using an evaporator, such as a thin-film evaporator described in Patent Documents described above, and thus mixed into the bottom product. Note that, in the reaction, when reduction of the remained amount of unreacted compound represented by Formula (b) is attempted by using an excessively large amount of an epoxidizing agent, such as organic peracid, for the compound represented by Formula (b) which is the raw material, the amount of the byproduct of the compound represented by Formula (d) is increased. Conversely, when the used amount of the epoxidizing agent, such as organic peracid, is reduced to reduce the amount of byproduct of the compound represented by Formula (d), the remained amount of the unreacted compound represented by Formula (b) is increased. Patent Documents described above do not focus on presence of these impurities, and thus there are no description or suggestion on how to remove such impurities.

In the alicyclic epoxy compound product according to an embodiment of the present invention, the content of the compound represented by Formula (a) is preferably 0.3 wt. % or less, more preferably 0.2 wt. % or less, even more preferably 0.1 wt. % or less, and particularly preferably 0.05 wt. % or less (e.g., 0.02 wt. % or less). Furthermore, the content of the compound represented by Formula (b) is preferably 1.0 wt. % or less, more preferably 0.8 wt. % or less, even more preferably 0.5 wt. % or less, and particularly preferably 0.2 wt. % or less (e.g., 0.1 wt. % or less). The content of the compound represented by Formula (c) is preferably 0.3 wt. % or less, more preferably 0.2 wt. % or less, even more preferably 0.1 wt. % or less, and particularly preferably 0.05 wt. % or less (e.g., 0.03 wt. % or less). Furthermore, the content of the compound represented by Formula (d) is preferably 0.6 wt. % or less, more preferably 0.3 wt. % or less, even more preferably 0.2 wt. % or less, and particularly preferably 0.1 wt. % or less (e.g., 0.05 wt. % or less).

The alicyclic epoxy compound product according to an embodiment of the present invention has a low degree of coloration, and a Hazen color number (APHA) is, for example, 25 or less, preferably 20 or less, and particularly preferably 18 or less. Furthermore, the alicyclic epoxy compound product according to an embodiment of the present invention has excellent storage stability, and the percentage of increase of the Hazen color number (APHA) after the alicyclic epoxy compound product is stored at 30° C. for 1 month is less than 200%.

Method for Producing Alicyclic Epoxy Compound Product

The alicyclic epoxy compound product according to an embodiment of the present invention can be produced through the following. Note that either Process B and Process C may be performed before another.

Process A: a process of obtaining a reaction product (crude reaction solution) by epoxidizing 3-cyclohexenylmethyl methacrylate by an organic peracid (epoxidation).

Process B: a process of subjecting a reaction product (which may have been undergone a predetermined process) to removal of low-boiling fractions by distillation (removal of low-boiling fractions)

Process C: a process of subjecting a reaction product (which may have been undergone a predetermined process) to removal of high-boiling fractions by distillation (removal of high-boiling fractions)

Furthermore, after completion of Process A, before Process B (Process C in the case of performing in the order of Process C-Process B), a process of water washing the obtained reaction product (water washing) and/or a process of neutralizing the reaction product with an alkali (alkali neutralization treatment) may be provided. Furthermore, when Process B is performed in multiple stages, a process of washing with an alkali aqueous solution (alkali solution washing) may be provided in between the stages. Furthermore, before Process B or Process C, solvent removal may be provided to remove the solvent in the reaction product. This solvent removal corresponds to the removal of low-boiling fractions described in Patent Documents described above.

Epoxidation

The epoxidation is a process of forming 3,4-epoxycyclohexylmethyl methacrylate by reacting 3-cyclohexenylmethyl methacrylate represented by Formula (b) with an organic peracid as shown in the scheme below. In this process, a reaction product containing 3,4-epoxycyclohexylmethyl methacrylate represented by Formula (i) (crude reaction solution) can be obtained.

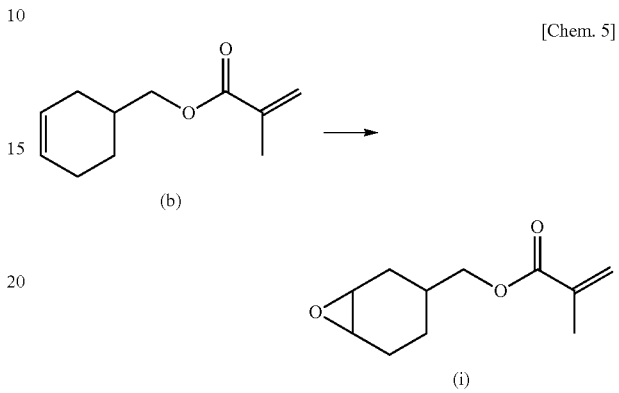

Examples of the organic peracid include performic acid, peracetic acid, perpropionic acid, m-chloroperbenzoic acid, trifluoroperacetic acid, and perbenzoic acid. These may be used in combination with a catalyst. As the catalyst, alkalis such as sodium carbonate and acids such as sulfuric acid can be used.

The used amount of the organic peracid is, for example, from 0.5 to 3 mol relative to 1 mol of 3-cyclohexenylmethyl methacrylate. When the used amount of the organic peracid is too small, problems of loss due to polymerization of raw materials or the target compound, or a great amount of cost in the case where unreacted 3-cyclohexenylmethyl methacrylate is recovered occur. On the other hand, when the used amount of the organic peracid is too large, problems such as increase in byproducts due to the excessive amount of the organic peracid occur.

The epoxidation reaction can be performed in the presence of a solvent. Examples of the solvent include aromatic hydrocarbons, such as benzene, toluene, xylene, ethylbenzene, isopropylbenzene, diethylbenzene, and p-cymene; alicyclic hydrocarbons such as cyclohexane, and decalin; aliphatic hydrocarbons, such as hexane, heptane, octane, nonane, and decane; monovalent alcohols, such as cyclohexanol, hexanol, heptanol, octanol, nonanol, furfuryl alcohol; ketones, such as acetone, methyl ethyl ketone, and cyclohexanone; esters, such as ethyl acetate, n-amyl acetate, cyclohexyl acetate, isoamyl propionate, and methyl benzoate; polyhydric alcohols and their derivatives (e.g. monoethers, monoesters, monoether monoesters, diethers, and diesters), such as ethylene glycol, propylene glycol, ethylene glycol monomethyl ether, ethylene glycol monomethyl ether acetate, ethylene glycol monoethyl ether, ethylene glycol monoethyl ether acetate, ethylene glycol dimethyl ether, diethylene glycol monomethyl ether, and diethylene glycol monoethyl ether; halogenated hydrocarbons, such as chloroform, methylene chloride, carbon tetrachloride, and chlorobenzene; and ethers, such as diethyl ether, diisopropyl ether, and dibutyl ether. One of these solvents can be used alone or two or more in combination.

The used amount of the solvent is, for example, approximately from 0.2 to 10 times the weight of 3-cyclohexenylmethyl methacrylate which is the raw material.

For the epoxidation reaction, as necessary, a stabilizer of an organic peracid (e.g. ammonium hydrogen phosphate, potassium pyrophosphate, 2-ethylhexyl pyrophosphate, potassium 2-ethylhexyl pyrophosphate, potassium tripolyphosphate, and 2-ethylhexyl tripolyphosphate) and a polymerization inhibitor (e.g., hydroquinone, hydroquinone monomethyl ether, p-benzoquinone, cresol, t-butylcatechol, 2,4-dimethyl-6-t-butylphenol, 2-t-butyl-4-methoxyphenol, 3-t-butyl-4-methoxyphenol, 2,6-di-t-butyl-p-cresol, 2,5-dihydroxy-p-quinone, piperidine, ethanolamine, α-nitroso-β-naphthol, diphenylamine, phenothiazine, N-nitroso-N-phenylhydroxylamine ammonium salt, N-nitroso-N-phenylhydroxylamine aluminum salt, N-nitroso-N,N-diphenylamine, dibutylhydroxytoluene, N,N-diethylhydroxylamine, 1-oxyl-2,2,6,6-tetramethylpiperidine, 1-oxyl-4-hydroxy-2,2,6,6-tetramethylpiperidine, 1-oxyl-4-acetamido-2,2,6,6-tetramethylpiperidine, 1-oxyl-4-benzoyloxy-2,2,6,6-tetramethylpiperidine, and bis(2,2,6,6-tetramethyl-4-piperidyl) sebacate) can be used.

The reaction temperature of the epoxidation reaction is, for example, from 0 to 70° C. The reaction atmosphere of the reaction above is not particularly limited as long as it does not inhibit the reaction. For example, any of an air atmosphere, a nitrogen atmosphere, and an argon atmosphere may be used. The epoxidation reaction may be performed while a molecular oxygen-containing gas is blown into the reaction system to suppress polymerization.

The reaction may be performed in any one of a continuous method (such as piston flow), a semi-batch method, or a batch method.

Water Washing

The water washing is to remove the organic peracid and organic acid which is a decomposition product of the organic peracid, contained in the reaction product obtained through the epoxidation, by water washing.

The used amount of water is, for example, approximately from 0.1 to 3 times (V/V) of the amount of the reaction product. An equilibrium extractor, such as a mixer-settler type; an extraction column; a centrifugal extractor; or the like can be used for the water washing.

Alkali Neutralization Treatment, Alkali Solution Washing

The alkali neutralization treatment and the alkali solution washing are processes of removing, for example, the organic peracid and the organic acid contained in the reaction product with an alkali. Examples of the alkali aqueous solution to be used include sodium hydroxide aqueous solutions, potassium hydroxide aqueous solutions, sodium carbonate aqueous solutions, and sodium hydrogencarbonate aqueous solutions. The used amount of the alkali aqueous solution is, for example, approximately from 0.1 to 10 times the weight of the reaction product (liquid to be treated) that is fed for the treatment.

For example, an equilibrium extractor such as a mixer-settler type, an extraction column, or a centrifugal extractor can be used for the alkali neutralization treatment and the alkali solution washing.

Solvent Removal

The solvent removal is a process of removing the solvent contained in the reaction product. The solvent removal typically uses an evaporator such as a thin-film evaporator or flushing can. The solvent removal is preferably performed in two stages to completely remove the solvent. The solvent removal of the first stage is preferably performed at a heating temperature of 50 to 100° C., and preferably in a range of 50 to 70° C. By the solvent removal of the first stage, a bottom liquid having a solvent concentration from 3 to 50 wt. % (preferably from 10 to 20 wt. %) can be obtained. The solvent removal of the second stage is preferably performed at a heating temperature of 50 to 100° C., and preferably in a range from 50 to 70° C. By the solvent removal of the second stage, a bottom liquid having a solvent concentration of 1 wt. % or less can be obtained.

In the solvent removal, to supplement the polymerization inhibitor and the stabilizer of organic peracid that have been lost by the water washing, alkali neutralization treatment, and alkali solution washing, an appropriate amount of these is preferably supplemented to the liquid to be treated that is subjected to the solvent removal treatment. Furthermore, in this process, a molecular oxygen-containing gas having polymerization prevention effect is preferably introduced to the evaporator. The location for introducing the molecular oxygen-containing gas can be freely selected but the molecular oxygen-containing gas is preferably blown through an extraction line of the bottom liquid.

Through the solvent removal, a crude product having a purity of 3,4-epoxycyclohexylmethyl methacrylate from 94 to 97 wt. % can be obtained.

Removal of Low-Boiling Fraction

The removal of low-boiling fractions is a process of distilling off components having lower boiling points than that of 3,4-epoxycyclohexylmethyl methacrylate, contained in the reaction product (e.g., such as a solvent, moisture, or low-boiling impurities). By this process, the content of the compounds represented by Formulas (a) to (c) above that are mixed to the alicyclic epoxy compound product can be reduced to extremely low. By reducing the content of the compounds represented by Formulas (a) to (c) above, coloration and coloration over time of the resulting alicyclic epoxy compound product can be suppressed, and physical properties, for example, especially transparency and heat resistance, and mechanical characteristics of a cured product obtained by curing a curable composition containing the alicyclic epoxy compound product can be enhanced.

As the distillation column in the removal of low-boiling fractions, for example, a tray tower or a packed tower can be used. The actual number of trays of the distillation column is typically 10 trays or more (e.g., from 10 to 100 trays), and preferably 20 trays or more (e.g., from 20 to 50 trays). The column top pressure is typically 1 mmHg or less, preferably 0.3 mmHg, and even more preferably 0.1 mmHg or less. The column top temperature is typically 100° C. or lower (e.g., from 40 to 100° C.), preferably 85° C. or lower (e.g., from 50 to 85° C.), and more preferably 80° C. or lower (e.g., from 50 to 80° C.). The column bottom temperature is typically 140° C. or lower (e.g., from 60 to 140° C.), preferably 130° C. or lower (e.g., from 70 to 130° C.), and more preferably 110° C. or lower (e.g., from 80 to 110° C.). The heating temperature is typically 150° C. or lower (e.g., from 70 to 150° C.), and preferably 130° C. or lower (e.g., from 90 to 130° C.). The reflux ratio is typically from 0.1 to 50, and preferably from 1 to 10.

By increasing the actual number of trays of the distillation column or increasing the reflux ratio, mixing of the compounds represented by Formulas (a) to (c) above into the product can be reduced. Furthermore, by lowering the column bottom temperature of the distillation column and the heating temperature, generation of polymers and other undesirable byproducts can be suppressed.

To suppress polymerization of, for example, the target compounds during the distillation, a polymerization inhibitor is preferably added to the liquid to be treated (distillation column supplied liquid) that is subjected to the removal of low-boiling fractions by distillation. As the polymerization inhibitor, those exemplified above can be used. Among these, examples of the preferred polymerization inhibitor include hydroquinone, p-benzoquinone, N-nitroso-N-phenylhydroxylamine ammonium salt, N-nitroso-N-phenylhydroxylamine aluminum salt, N-nitroso-N,N-diphenylamine, dibutylhydroxytoluene, 1-oxyl-2,2,6,6-tetramethylpiperidine, 1-oxyl-4-hydroxy-2,2,6,6-tetramethylpiperidine, 1-oxyl-4-acetamido-2,2,6,6-tetramethylpiperidine, 1-oxyl-4-benzoyloxy-2,2,6,6-tetramethylpiperidine, and bis(2,2,6,6-tetramethyl-4-piperidyl) sebacate. Note that the molecular oxygen-containing gas having a polymerization prevention effect may be blown into the distillation column; however, from the perspective of maintaining a high degree of vacuum, it is not preferable to blow the molecular oxygen-containing gas into the distillation column.

The used amount of the polymerization inhibitor is, for example, from 0.005 to 1 wt. %, preferably from 0.005 to 0.5 wt. %, even more preferably from 0.005 to 0.1 wt. %, and particularly preferably from 0.01 to 0.05 wt. %, relative to the amount of the liquid to be treated (distillation column supplied liquid).

The ratio of the column top distilled amount to the column bottom amount (former/latter) is, for example, from 2/98 to 20/80, preferably from 5/95 to 15/85, and even more preferably from 7/93 to 13/87.

In the removal of low-boiling fractions, by distilling the component having a boiling point that is lower than that of 3,4-epoxycyclohexylmethyl methacrylate from the distillation column supplied liquid from the column top, the 3,4-epoxycyclohexylmethyl methacrylate or a mixture of the 3,4-epoxycyclohexylmethyl methacrylate and components having higher boiling points than that of the 3,4-epoxycyclohexylmethyl methacrylate can be obtained as, for example, a bottom liquid.

Removal of High-Boiling Fraction

The removal of high-boiling fractions is a process of separating and removing components having higher boiling points than that of 3,4-epoxycyclohexylmethyl methacrylate, contained in the reaction product from, for example, the column bottom. By this process, the amounts of the compound represented by Formula (d) above and polymers that are mixed to the alicyclic epoxy compound product can be reduced to extremely low. By reducing the content of the compound represented by Formula (d) above and polymers, physical properties, for example, especially transparency and heat resistance, and mechanical characteristics of a cured product of a curable composition containing the obtained alicyclic epoxy compound product can be enhanced.

As the distillation column in the removal of high-boiling fractions, for example, a tray tower or a packed tower can be used. The actual number of trays of the distillation column is typically 10 trays or more (e.g., from 10 to 100 trays), and preferably 20 trays or more (e.g., from 20 to 50 trays). The column top pressure is typically 1 mmHg or less, preferably 0.3 mmHg, and even more preferably 0.1 mmHg or less. The column top temperature is typically 100° C. or lower (e.g., from 40 to 100° C.), preferably 85° C. or lower (e.g., from 50 to 85° C.), and more preferably 80° C. or lower (e.g., from 50 to 80° C.). The column bottom temperature is typically 140° C. or lower (e.g., from 60 to 140° C.), preferably 120° C. or lower (e.g., from 80 to 120° C.), and more preferably 110° C. or lower (e.g., from 80 to 110° C.). The heating temperature is typically 150° C. or lower (e.g., from 70 to 150° C.), preferably 140° C. or lower (e.g., from 90 to 140° C.), and more preferably 130° C. or lower (e.g., from 90 to 130° C.). The reflux ratio is typically from 0.1 to 50, and preferably from 1 to 10.

By increasing the actual number of trays of the distillation column or increasing the reflux ratio, mixing of the compound represented by Formula (d) above and polymers into the product can be reduced. Furthermore, by lowering the column bottom temperature of the distillation column and the heating temperature, generation of polymers and other undesirable byproducts can be suppressed.

To suppress polymerization of, for example, the target compounds during the distillation, a polymerization inhibitor may be added to the liquid to be treated (distillation column supplied liquid) that is subjected to the removal of high-boiling fractions by distillation. As the polymerization inhibitor, those exemplified in the section of Removal of low-boiling fractions by distillation described above can be used. Note that the molecular oxygen-containing gas having a polymerization prevention effect may be blown into the distillation column; however, from the perspective of maintaining a high degree of vacuum, it is not preferable to blow the molecular oxygen-containing gas into the distillation column.

The used amount of the polymerization inhibitor is, for example, from 0.005 to 1 wt. %, preferably from 0.005 to 0.5 wt. %, even more preferably from 0.005 to 0.1 wt. %, and particularly preferably from 0.01 to 0.05 wt. %, relative to the amount of the liquid to be treated (distillation column supplied liquid).

The ratio of the column top distilled amount to the column bottom amount (former/latter) is, for example, from 80/20 to 98/2, preferably from 85/15 to 95/5, and even more preferably from 87/13 to 93/7.

In the removal of high-boiling fractions, by discharging the component having a boiling point that is higher than that of 3,4-epoxycyclohexylmethyl methacrylate from the distillation column supplied liquid from the column bottom, the 3,4-epoxycyclohexylmethyl methacrylate or a mixture of the 3,4-epoxycyclohexylmethyl methacrylate and components having lower boiling points than that of the 3,4-epoxycyclohexylmethyl methacrylate can be obtained as, for example, a bottom liquid.

As described above, by subjecting the reaction product to the treatment for removal of low-boiling fractions and the treatment for removal of high-boiling fractions, the alicyclic epoxy compound product having a high purity of 3,4-epoxycyclohexylmethyl methacrylate and a small content of particular impurities can be obtained.

Curable Composition

The curable composition according to an embodiment of the present invention contains the alicyclic epoxy compound product (high-purity 3,4-epoxycyclohexylmethyl methacrylate).

The curable composition according to an embodiment of the present invention contains, as the curable compound (A), 3,4-epoxycyclohexylmethyl methacrylate contained in the alicyclic epoxy compound product described above, but may contain one or two or more other curable compounds besides the 3,4-epoxycyclohexylmethyl methacrylate.

Examples of such other curable compounds include a compound (A1) having a cationically polymerizable group and a radically polymerizable group besides the 3,4-epoxycyclohexylmethyl methacrylate, a cationically polymerizable compound (A2) having no radically polymerizable group, and a radically polymerizable compound (A3) having no cationically polymerizable group.

Examples of the compound (A1) having a cationically polymerizable group and a radically polymerizable group besides the 3,4-epoxycyclohexylmethyl methacrylate include polymerizable unsaturated compounds (such as (meth)acrylate derivatives) containing an epoxy group-containing alicyclic carbon ring such as a 3,4-epoxycyclohexane ring, such as 3,4-epoxycyclohexyl (meth)acrylate, 3,4-epoxycyclohexylmethyl acrylate, 2-(3,4-epoxycyclohexyl)ethyl (meth)acrylate, 2-(3,4-epoxycyclohexylmethyloxy)ethyl (meth)acrylate, and 3-(3,4-epoxycyclohexylmethyloxy)propyl (meth)acrylate; polymerizable unsaturated compound (such as (meth)acrylate derivatives) containing a 5,6-epoxy-2-bicyclo[2.2.1]heptane ring, such as 5,6-epoxy-2-bicyclo[2.2.1]heptyl (meth)acrylate; and polymerizable unsaturated compounds (such as (meth)acrylate derivatives) containing a 3,4-epoxytricyclo[5.2.1.0$^{2,6}$]decane ring, such as epoxidized dicyclopentenyl (meth)acrylate [3,4-epoxytricyclo[5.2.1.0$^{2,6}$]decan-9-yl (meth)acrylate, 3,4-epoxytricyclo[5.2.1.0$^{2,6}$]decan-8-yl (meth)acrylate, or a mixture of these], epoxidized dicyclopentenyloxyethyl (meth)acrylate [2-(3,4-epoxytricyclo[5.2.1.0$^{2,6}$]decan-9-yloxy)ethyl (meth) acrylate, 2-(3,4-epoxytricyclo[5.2.1.0$^{2,6}$]decan-8-yloxy) ethyl (meth)acrylate, or a mixture of these], epoxidized dicyclopentenyloxybutyl (meth)acrylate, and epoxidized dicyclopentenyloxyhexyl (meth)acrylate.

As the compound (A1) having a cationically polymerizable group and a radically polymerizable group besides the 3,4-epoxycyclohexylmethyl methacrylate, a single type or a combination of two or more types can be used.

Examples of the cationically polymerizable compound (A2) having no radically polymerizable group include epoxy compounds, oxetane compounds, and vinyl ether compounds.

The epoxy compound includes an alicyclic epoxy compound, an aromatic epoxy compound, and an aliphatic epoxy compound.

The alicyclic epoxy compound includes the following compounds:

(1) a compound having an epoxy group (which may be referred to as an "alicyclic epoxy group" in the present specification, and the alicyclic epoxy group includes, for example, a cyclohexene oxide group) composed of two adjacent carbon atoms and an oxygen atom that constitute an alicyclic ring in the molecule (excluding 3,4-epoxycyclohexylmethyl methacrylate);

(2) a compound in which an epoxy group is directly bonded to an alicyclic ring by a single bond; and (3) a compound having an alicyclic ring and a glycidyl ether group in the molecule (a glycidyl ether epoxy compound).

Examples of the compound (I) having an alicyclic epoxy group include a compound represented by Formula (1) below:

[Chem. 6]

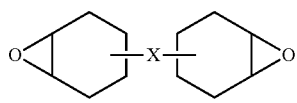

(1)

where X represents a single bond or a linking group.

In Formula (1) above, X represents a single bond or a linking group (a divalent group having one or more atoms). Examples of the linking group include a divalent hydrocarbon group, an epoxidized alkenylene group in which some or all of carbon-carbon double bonds are epoxidized, a carbonyl group, an ether bond, an ester bond, a carbonate group, an amide group, and a linked group in which a plurality of the above groups are linked. Note that, in Formula (1), a substituent (e.g. an alkyl group) may be bonded to a cyclohexene oxide group.

Examples of the divalent hydrocarbon group include a linear or branched alkylene group having from 1 to 18 carbon atoms and a divalent alicyclic hydrocarbon group. Examples of the linear or branched alkylene group having from 1 to 18 carbon atoms include a methylene group, a methylmethylene group, a dimethylmethylene group, an ethylene group, a propylene group, and a trimethylene group. Examples of the divalent alicyclic hydrocarbon group include a cycloalkylene group (including a cycloalkylidene group), such as a 1,2-cyclopentylene group, a 1,3-cyclopentylene group, a cyclopentylidene group, a 1,2-cyclohexylene group, a 1,3-cyclohexylene group, a 1,4-cyclohexylene group, and a cyclohexylidene group.

Examples of the alkenylene group in the epoxidized alkenylene group in which one, some, or all carbon-carbon double bond(s) is (are) epoxidized (which may be referred to as the "epoxidized alkenylene group") include a linear or branched alkenylene group having from 2 to 8 carbon atoms, such as a vinylene group, a propenylene group, a 1-butenylene group, a 2-butenylene group, a butadienylene group, a pentenylene group, a hexenylene group, a heptenylene group, and an octenylene group. In particular, the epoxidized alkenylene group is preferably an epoxidized alkenylene group in which all of the carbon-carbon double bond(s) is/are epoxidized and more preferably an epoxidized alkenylene group having from 2 to 4 carbon atoms in which all of the carbon-carbon double bond(s) is/are epoxidized.

Representative examples of the compound represented by Formula (1) above include (3,4,3',4'-diepoxy)bicyclohexyl, bis(3,4-epoxycyclohexylmethyl)ether, 1,2-epoxy-1,2-bis(3,4-epoxycyclohexane-1-yl)ethane, 2,2-bis(3,4-epoxycyclohexane-1-yl)propane, 1,2-bis(3,4-epoxycyclohexane-1-yl) ethane, and compounds represented by Formulas (1-1) to (1-7) below. L in Formula (1-4) below is an alkylene group having from 1 to 8 carbon atoms and is preferably, among these alkylene groups, a linear or branched alkylene group having from 1 to 3 carbon atoms, such as a methylene group, an ethylene group, a propylene group, or an isopropylene group. In Formulas (1-4) and (1-6) below, n$^1$ and n$^2$ each represent an integer from 1 to 30.

[Chem. 7]

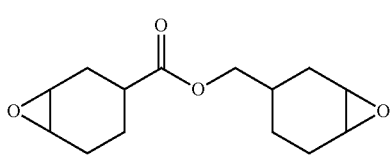

(1-1)

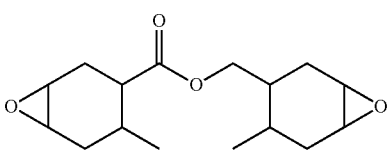

(1-1')

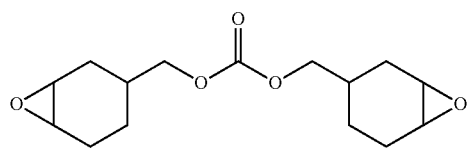

(1-2)

-continued (1-3)
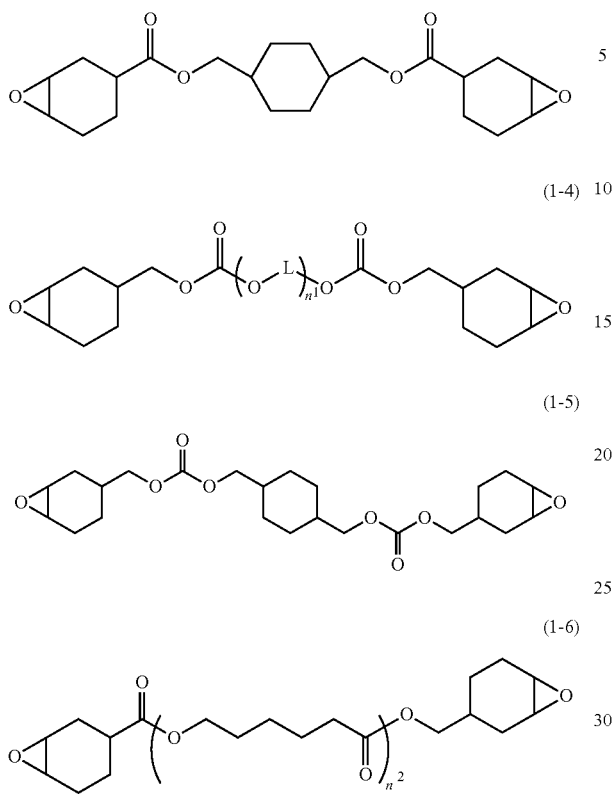
(1-4)

(1-5)

(1-6)

(1-7)

ⓘ indicates text missing or illegible when filed

Examples of the compound (1) having the alicyclic epoxy group also includes, in addition to the compound represented by Formula (1) above, compounds having three or more alicyclic epoxy groups in the molecule, represented by Formulas (1-8) and (1-9) below, or the compound having one alicyclic epoxy group in the molecule, represented by Formula (1-10) below. In Formulas (1-8) and (1-9), $n^3$ to $n^8$ each represent an integer from 1 to 30.

[Chem. 8]

(1-8)
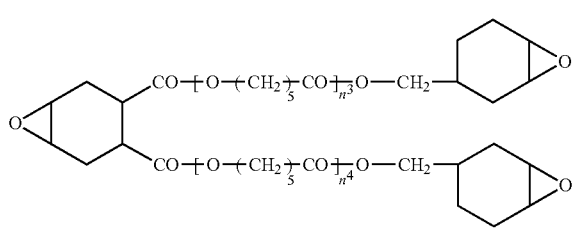

-continued (1-9)
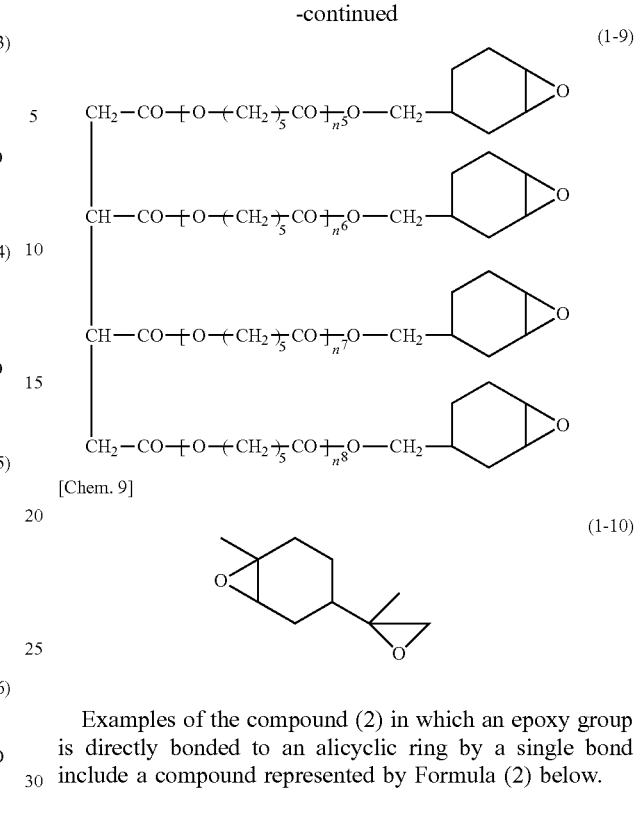

[Chem. 9]

(1-10)
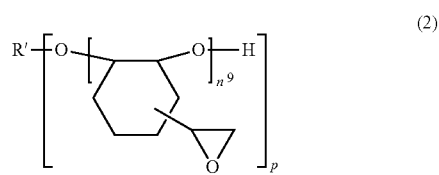

Examples of the compound (2) in which an epoxy group is directly bonded to an alicyclic ring by a single bond include a compound represented by Formula (2) below.

[Chem. 10]

$$R'\text{-}\!\!\left[\text{O}\text{-}\!\!\left[\begin{array}{c}\phantom{x}\\ \phantom{x}\end{array}\right]_{n^9}\!\!\text{-}\text{O}\right]_p\!\!\text{-}H \quad (2)$$

In Formula (2), R' is a group obtained by removing p hydroxy groups from a structural formula of a p-hydric alcohol (p-valent organic group), and p and $n^9$ each represent a natural number. Examples of the p-hydric alcohol [R' $(OH)_p$] include polyhydric alcohols (such as polyhydric alcohols having from 1 to 15 carbon atoms), such as 2,2-bis(hydroxymethyl)-1-butanol. Here, p is preferably from 1 to 6, and $n^9$ is preferably from 1 to 30. In the case where p is 2 or greater, $n^9$ moieties of a group within [ ] (within the outer square brackets) may be the same or different. Examples of the compound represented by Formula (2) above specifically include a 1,2-epoxy-4-(2-oxiranyl)cyclohexane adduct of 2,2-bis(hydroxymethyl)-1-butanol (e.g., such as "EHP- E3150 (trade name)" (available from Daicel Corporation)).

Examples of the glycidyl ether epoxy compound (3) include glycidyl ethers of alicyclic alcohols (in particular, alicyclic polyhydric alcohols). More in particular, examples of the glycidyl ether epoxy compounds include a hydrogenated bisphenol A epoxy compound, a hydrogenated bisphenol F epoxy compound, a hydrogenated biphenol epoxy compound, a hydrogenated phenol novolac epoxy compound, and a hydrogenated cresol novolac epoxy compound.

Examples of the aromatic epoxy compounds include a bisphenol A epoxy compound, a bisphenol F epoxy compound, a biphenol epoxy compound, a phenol novolac epoxy compound, and a cresol novolac epoxy compound.

Examples of the aliphatic epoxy compounds include glycidyl ethers of q-hydric alcohols having no cyclic structure (q is a natural number); glycidyl esters of monovalent or polyvalent carboxylic acids (e.g., such as acetic acid, propionic acid, butyric acid, stearic acid, adipic acid, sebacic acid, maleic acid, or itaconic acid); epoxidized materials of fats and oils having a double bond, such as epoxidized linseed oil, epoxidized soybean oil, and epoxidized castor oil; and epoxidized materials of polyolefins (including polyalkadienes), such as epoxidized polybutadiene.

Examples of the oxetane compounds may include 3,3-bis (vinyloxymethyl)oxetane, 3-ethyl-3-hydroxymethyloxetane, 3-ethyl-3-(2-ethylhexyloxymethyl)oxetane, 3-ethyl-3-(hydroxymethyl)oxetane, 3-ethyl-3-[(phenoxy)methyl] oxetane, 3-ethyl-3-(hexyloxymethyl)oxetane, 3-ethyl-3-(chloromethyl)oxetane, 3,3-bis(chloromethyl)oxetane, 1,4-bis[(3-ethyl-3-oxetanylmethoxy)methyl]benzene, bis([1-ethyl(3-oxetanyl)]methyl)ether, 4,4'-bis[(3-ethyl-3-oxetanyl)methoxymethyl]bicyclohexyl, 4,4'-bis[(3-ethyl-3-oxetanyl)methoxymethyl]biphenyl, 1,4-bis[(3-ethyl-3-oxetanyl)methoxymethyl]cyclohexane, 1,4-bis([(3-ethyl-3-oxetanyl)methoxy]methyl]benzene, 3-ethyl-3{[(3-ethyloxetan-3-yl) methoxy]methyl}oxetane, and xylylenebisoxetane.

Examples of the vinyl ether compounds include aryl vinyl ethers, such as phenyl vinyl ether; alkyl vinyl ethers, such as n-butyl vinyl ether and n-octyl vinyl ether; cycloalkyl vinyl ethers, such as cyclohexyl vinyl ether; vinyl ethers having a hydroxyl group, such as 2-hydroxyethyl vinyl ether, diethylene glycol monovinyl ether, and 2-hydroxybutyl vinyl ether; and polyfunctional vinyl ethers, such as hydroquinone divinyl ether, 1,4-butanediol divinyl ether, cyclohexane divinyl ether, cyclohexanedimethanol divinyl ether, ethylene glycol divinyl ether, diethylene glycol divinyl ether, and triethylene glycol divinyl ether.

As the cationically polymerizable compound (A2) having no radically polymerizable group, a single type or a combination of two or more types can be used.

Examples of the radically polymerizable compound (A3) having no cationically polymerizable group include alkyl (meth)acrylate [e.g. C1-10 alkyl (meth)acrylate] such as methyl (meth)acrylate, ethyl (meth)acrylate, propyl (meth) acrylate, butyl (meth)acrylate, pentyl (meth)acrylate, hexyl (meth)acrylate, 2-ethylhexyl (meth)acrylate, and dodecyl (meth)acrylate; (meth)acrylate having an aromatic ring structure in the molecule, such as benzyl (meth)acrylate; (meth)acrylate having an alicyclic structure, including (meth)acrylate having a cyclohexane ring, such as cyclohexyl (meth)acrylate, cyclohexylmethyl (meth)acrylate, 2-(cyclohexyl)ethyl (meth)acrylate, 2-(cyclohexylmethyloxy)ethyl (meth)acrylate, and 3-(cyclohexylmethyloxy)propyl (meth)acrylate; (meth)acrylate having a 2-bicyclo[2.2.1] heptane ring, such as 2-bicyclo[2.2.1]heptyl (meth)acrylate; (meth)acrylate having an adamantane ring, such as 1-adamantyl (meth)acrylate; (meth)acrylate having a tricyclo [5.2.1.0$^{2,6}$]decane ring, such as dicyclopentanyl (meth)acrylate {tricyclo[5.2.1.0$^{2,6}$]decan-9-yl (meth)acrylate, tricyclo [5.2.1.0$^{2,6}$]decan-8-yl (meth)acrylate, or a mixture of these}, dicyclopentenyl (meth)acrylate {tricyclo[5.2.1.0$^{2,6}$]dec-3-en-9-yl (meth)acrylate, tricyclo[5.2.1.0$^{2,6}$]dec-3-en-8-yl (meth)acrylate, or a mixture of these}, dicyclopentenyloxyethyl (meth)acrylate {2-(tricyclo[5.2.1.0$^{2,6}$]decan-9-yloxy) ethyl (meth)acrylate, 2-(tricyclo[5.2.1.0$^{2,6}$]decan-8-yloxy) ethyl (meth)acrylate, or a mixture of these}, dicyclopentenyloxybutyl (meth)acrylate, and dicyclopentenyloxyhexyl (meth)acrylate; styrene-based compounds, such as styrene, vinyl toluene, α-methyl styrene, and vinyl naphthalene; vinyl ether compounds, such as methyl vinyl ether, butyl vinyl ether, and phenyl vinyl ether; (meth) acrylate having a hydroxy group, such as 2-hydroxyethyl (meth)acrylate, hydroxypropyl (meth)acrylate, and hydroxybutyl (meth)acrylate; alkoxypolyalkylene glycol (meth)acrylate, such as methoxydiethylene glycol (meth) acrylate, ethoxydiethylene glycol (meth)acrylate, isooctyloxydiethylene glycol (meth)acrylate, methoxytriethylene glycol (meth)acrylate, and methoxypolyethylene glycol (meth)acrylate; (meth)acrylate having an amino group, such as 2-aminoethyl (meth)acrylate; heterocyclic compounds having a vinyl group (e.g., nitrogen-containing heterocyclic compounds), such as 2-vinylpyrrolidone; α,β-unsaturated carboxylic acid, such as acrylic acid, methacrylic acid, itaconic acid, crotonic acid, maleic acid, and fumaric acid, and acid anhydrides thereof (e.g., maleic anhydride, itaconic anhydride); and polyfunctional (meth)acrylate.

As the radically polymerizable compound (A3) having no cationically polymerizable group, a single type or a combination of two or more types can be used.

The proportion of the 3,4-epoxy cyclohexylmethyl methacrylate in the total amount (100 wt. %) of the curable compound (A) contained in the curable composition is, for example, 10 wt. % or greater (e.g., from 10 to 100 wt. %), preferably 30 wt. % or greater, more preferably 50 wt. % or greater, and even more preferably 80 wt. % or greater.

The curable composition according to an embodiment of the present invention preferably contains, in addition to the curable compound (A), for example, a curing agent (B), a curing accelerator (C), or a curing catalyst (D).

The proportion of the total content of the curable compound (A), the curing agent (B), and the curing accelerator (C) relative to the total amount of the curable composition according to an embodiment of the present invention is, for example, 5 wt. % or greater, preferably 30 wt. % or greater, more preferably 60 wt. % or greater, even more preferably 80 wt. % or greater, particularly preferably 90 wt. % or greater, and especially preferably 95 wt. % or greater.

Furthermore, the proportion of the total content of the curable compound (A) and the curing catalyst (D) relative to the total amount of the curable composition according to an embodiment of the present invention is, for example, 5 wt. % or greater, preferably 30 wt. % or greater, more preferably 60 wt. % or greater, even more preferably 80 wt. % or greater, particularly preferably 90 wt. % or greater, and especially preferably 95 wt. % or greater.

Thus, the content of the compound other than the curable compound (A), the curing agent (B), the curing accelerator (C), and the curing catalyst (D) relative to the total amount of the curable composition according to an embodiment of the present invention is, for example, 95 wt. % or less, preferably 50 wt. % or less, and more preferably 40 wt. % or less.

Curing Agent (B)

Examples of the curing agent (B) that can be used include curing agents well-known or commonly used as curing agents for epoxy resins, such as acid anhydrides (acid anhydride-based curing agents), amines (amine-based curing agents), polyamide resins, imidazoles (imidazole-based curing agents), polymercaptans (polymercaptane-based curing agents), phenols (phenol-based curing agents), polycarboxylic acids, dicyandiamides, and organic acid hydrazides. One of these can be used alone or two or more in combination.

Examples of the acid anhydrides include methyltetrahydrophthalic anhydrides (such as 4-methyltetrahydrophthalic anhydride and 3-methyltetrahydrophthalic anhydride), methylhexahydrophthalic anhydride (such as 4-methylhexahydrophthalic anhydride and 3-methylhexahydrophthalic anhydride), dodecenyl succinic anhydride, methyl endomethylene tetrahydrophthalic anhydride, phthalic anhydride, maleic anhydride, tetrahydrophthalic anhydride, hexahydrophthalic anhydride, methylcyclohexene dicarboxylic anhydride, pyromellitic anhydride, trimellitic anhydride, benzophenone tetracarboxylic anhydride, nadic anhydride, methylnadic anhydride, hydrogenated methylnadic anhydride, 4-(4-methyl-3-pentenyl)tetrahydrophthalic anhydride, succinic anhydride, adipic anhydride, sebacic anhydride, dodecanedioic anhydride, methylcylohexene tetracarboxylic anhydride, vinyl ether-maleic anhydride copolymers, and alkyl styrene-maleic anhydride copolymers. Among these acid anhydrides, acid anhydrides that are liquid at 25° C. (e.g., such as methyltetrahydrophthalic anhydride, methylhexahydrophthalic anhydride, dodecenyl succinic anhydride, and methyl endomethylene tetrahydrophthalic anhydride) are preferred in terms of handleability.

Examples of the amines include aliphatic polyamines, such as ethylenediamine, diethylenetriamine, triethylenetetramine, tetraethylenepentamine, dipropylenediamine, diethylaminopropylamine, and polypropylenetriamine; alicyclic polyamines, such as menthenediamine, isophoronediamine, bis(4-amino-3-methyldicyclohexyl)methane, diaminodicyclohexylmethane, bis(aminomethyl)cyclohexane, N-aminoethyl piperazine, and 3,9-bis(3-aminopropyl)-3,4,8,10-tetraoxaspiro[5,5]undecane; mononuclear polyamines, such as m-phenylenediamine, p-phenylenediamine, tolylene-2,4-diamine, tolylene-2,6-diamine, mesitylene-2,4-diamine, 3,5-diethyltolylene-2,4-diamine, and 3,5-diethyltolylene-2,6-diamine; and aromatic polyamines, such as biphenylenediamine, 4,4-diaminodiphenylmethane, 2,5-naphtylenediamine, and 2,6-naphtylenediamine.

Examples of the polyamide resins include polyamide resins having either one of a primary amino group or a secondary amino group or both in the molecule.

Examples of the imidazoles include 2-methylimidazole, 2-ethyl-4-methylimidazole, 2-undecylimidazole, 2-heptadecylimidazole, 2-phenylimidazole, 1-benzyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-undecylimidazolium trimellitate, 1-cyanoethyl-2-phenylimidazolium trimellitate, 2-methylimidazolium isocyanurate, 2-phenylimidazolium isocyanurate, 2,4-diamino-6-[2-methylimidazolyl-(1)]-ethyl-s-triazine, and 2,4-diamino-6-[2-ethyl-4-methylimidazolyl-(1)]-ethyl-s-triazine.

Examples of the polymercaptans include liquid polymercaptans and polysulfide resins.

Examples of the phenols include aralkyl resins, such as novolac phenolic resins, novolac cresol resins, p-xylylene-modified phenolic resins, and p-xylylene/m-xylylene-modified phenolic resins; terpene-modified phenolic resins; dicyclopentadiene-modified phenolic resins, and triphenolpropane.

Examples of the polycarboxylic acids include adipic acid, sebacic acid, terephthalic acid, trimellitic acid, and carboxy group-containing polyester.

The curing agent (B) is preferably an acid anhydride (acid anhydride curing agent) in terms of heat resistance and transparency of the resulting cured product, and a commercially available product can be used, such as "RIKACID MH-700 (trade name)" and "RIKACID MH-700F (trade name)" (both available from New Japan Chemical Co., Ltd.), and "HN-5500 (trade name)" (available from Hitachi Chemical Co., Ltd.).

The content (an amount to be blended) of the curing agent (B) is preferably from 50 to 200 parts by weight and more preferably from 80 to 150 parts by weight per 100 parts by weight of a total amount of compounds having an epoxy group included in the curable composition. More specifically, an acid anhydride, when used as the curing agent (B), is preferably used in a proportion from 0.5 to 1.5 equivalents per equivalent of epoxy groups in all the compounds having an epoxy group included in the curable composition according to an embodiment of the present invention. Making the content of the curing agent (B) at 50 parts by weight or greater allows the curing reaction to sufficiently proceed and tends to improve toughness of the resulting cured product. On the other hand, making the content of the curing agent (B) at 200 parts by weight or less prevents discoloration, tending to provide a cured product excellent in hue.

Curing Accelerator (C)

The curable composition according to an embodiment of the present invention, when contains the curing agent (B), preferably further contains the curing accelerator (C). The curing accelerator (C) has an effect of accelerating the reaction rate when a compound having an epoxy group (oxiranyl group) reacts with the curing agent (B).

Examples of the curing accelerator (C) include 1,8-diazabicyclo[5.4.0]undecene-7 (DBU) or salts thereof (e.g., such as a phenol salt, an octylate salt, a p-toluene sulfonate salt, a formate salt, and a tetraphenylborate salt); 1,5-diazabicyclo[4.3.0]nonene-5 (DBN) or salts thereof (e.g., such as a phenol salt, an octylate salt, a p-toluene sulfonate salt, a formate salt, and a tetraphenylborate salt); tertiary amines, such as benzyldimethylamine, 2,4,6-tris(dimethylaminomethyl) phenol, and N,N-dimethylcyclohexylamine; imidazoles, such as 2-ethyl-4-methylimidazole and 1-cyanoethyl-2-ethyl-4-methylimidazole; phosphoric esters; phosphines, such as triphenylphosphine and tris(dimethoxy)phosphine; phosphonium compounds, such as tetraphenylphosphonium tetra(p-tolyl)borate; organometallic salts, such as zinc octylate, tin octylate, and zinc stearate; and metal chelates, such as aluminum acetylacetone complex. One of these can be used alone or two or more in combination.

As the curing accelerator (C), a commercially available product can be used, such as, for example, "U-CAT SA 506 (trade name)", "U-CAT SA 102 (trade name)", "U-CAT 5003 (trade name)", "U-CAT 18X (trade name)", and "U-CAT 12XD (trade name)" (under development) (the above available from San-Apro Ltd.); "TPP-K (trade name)" and "TPP-MK (trade name)" (the above available from Hokko Chemical Industry Co., Ltd.); and "PX-4ET (trade name)" (available from Nippon Chemical Industrial Co., Ltd.).

The content (an amount to be blended) of the curing accelerator (C) is preferably from 0.01 to 5 parts by weight, more preferably from 0.02 to 3 parts by weight, and even more preferably from 0.03 to 3 parts by weight per 100 parts by weight of the curing agent (B). Making the content of the curing accelerator (C) at 0.01 parts by weight or greater readily provides a further efficient curing accelerating effect. On the other hand, making the content of the curing accelerator (C) at 5 parts by weight or less prevents discoloration, and readily provide a cured product excellent in hue.

Curing Catalyst (D)

The curable composition according to an embodiment of the present invention may contain the curing catalyst (D) in place of the curing agent (B). The curing catalyst (D) has a function to cure the curable composition by initiating and/or accelerating the curing reaction (polymerization reaction) of a curable (polymerizable) compound, such as 3,4-epoxycyclohexylmethyl methacrylate. Examples of the curing catalyst (D) include cationic polymerization initiators (such as photocationic polymerization initiators and thermal cationic polymerization initiators), which initiate polymerization by generating cationic species upon, for example, light irradiation or heat treatment; Lewis acid-amine complexes; Bronsted acid salts; imidazoles; and radical polymerization initiators (photoradical polymerization initiators, thermal radical polymerization initiators). One of these can be used alone or two or more in combination.

Examples of the photocationic polymerization initiators include hexafluoroantimonate salts, pentafluorohydroxyantimonate salts, hexafluorophosphate salts, and hexafluoroalcenate salts, and more specifically include sulfonium salts (in particular, triarylsulfonium salts), such as triarylsulfonium hexafluorophosphate (e.g., such as p-phenylthiophenyl diphenylsulfonium hexafluorophosphate) and triarylsulfonium hexafluoroantimonate; iodonium salts, such as diaryliodonium hexafluorophosphate, diaryliodonium hexafluoroantimonate, bis(dodecylphenyl)iodonium tetrakis(pentafluorophenyl)borate, and iodonium [4-(4-methylphenyl-2-methylpropyl)phenyl]hexafluorophosphate; phosphonium salts, such as tetrafluorophosphonium hexafluorophosphate; and pyridinium salts, such as N-hexylpyridinium tetrafluoroborate. In addition, as the photocationic polymerization initiator, a commercially available product can be preferably used, such as, for example, "UVACURE1590 (trade name)" (available from Daicel-Cytec Co., Ltd.); "CD-1010 (trade name)", "CD-1011 (trade name)", and "CD-1012 (trade name)" (the above available from Sartomer USA); "Irgacure 264 (trade name)" (available from BASF); and "CIT-1682 (trade name)" (Nippon Soda Co., Ltd.).

Examples of the thermal cationic polymerization initiators include aryldiazonium salts, aryliodonium salts, arylsulfonium salts, and allene-ion complexes. A commercially available product can be preferably used, such as, for example, "PP-33 (trade name)", "CP-66 (trade name)", and "CP-77 (trade name)" (the above available from Adeka Corporation); "FC-509 (trade name)" (available from 3M); "UVE1014 (trade name)" (available from G.E.); "SAN-AID SI-60L (trade name)", "SAN-AID SI-80L (trade name)", "SAN-AID SI-100L (trade name)", "SAN-AID SI-110L (trade name)", and "SAN-AID SI-150L (trade name)" (the above available from Sanshin Chemical Industry Co., Ltd.); and "CG-24-61 (trade name)" (available from BASF).

Examples of the Lewis acid-amine complexes include BF3-n-hexylamine, BF3-monoethylamine, BF3-benzylamine, BF3-diethylamine, BF3-pyperidine, BF3-triethylamine, BF3-aniline, BF4-n-hexylamine, BF4-monoethylamine, BF4-benzylamine, BF4-diethylamine, BF4-pyperidine, BF4-triethylamine, BF4-aniline, PF5-ethylamine, PF5-isopropylamine, PF5-butylamine, PF5-laurylamine, PF5-benzylamine, and AsF5-laurylamine.

Examples of the Bronsted acid salts include aliphatic sulfonium salts, aromatic sulfonium salts, iodonium salts, and phosphonium salts.

Examples of the imidazoles include 2-methylimidazole, 2-ethyl-4-methylimidazole, 2-undecylimidazole, 2-heptadecylimidazole, 2-phenylimidazole, 1-benzyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-undecylimidazolium trimellitate, 1-cyanoethyl-2-phenylimidazolium trimellitate, 2-methylimidazolium isocyanurate, 2-phenylimidazolium isocyanurate, 2,4-diamino-6-[2-methylimidazolyl-(1)]-ethyl-s-triazine, and 2,4-diamino-6-[2-ethyl-4-methylimidazolyl-(1)]-ethyl-s-triazine.

As the radical polymerization initiator, a thermal radical polymerization initiator or a photoradical polymerization initiator can be used. Examples of the thermal radical polymerization initiator include azo compounds such as 2,2'-azobisisobutyronitrile, 2,2'-azobis(2,4-dimethylvaleronitrile), 2,2'-azobis(4-methoxy-2,4-dimethylvaleronitrile), dimethyl-2,2'-azobis(2-methylpropionate), dimethyl 2,2'-azobis(isobutyrate), diethyl-2,2'-azobis(2-methylpropionate), and dibutyl-2,2'-azobis(2-methylpropionate), organic peroxides such as benzoyl peroxide, lauroyl peroxide, t-butylperoxypivalate, and 1,1-bis t-butylperoxy) cyclohexane, and hydrogen peroxide. When a peroxide is used as the radical polymerization initiator, the peroxide may be combined with a reducing agent and used as a redox initiator. Furthermore, a radical polymerization initiator and a chain transfer agent may be used in combination.

Furthermore, as the photoradical polymerization initiator, a single type or a mixture of, for example, benzophenones such as benzophenone; acetophenone benzyl, benzyldimethyl ketone; benzoins such as benzoin, benzoin methyl ether, benzoin ethyl ether, benzoin isopropyl ether; acetophenones such as dimethoxyacetophenone, dimethoxy phenylacetophenone, diethoxyacetophenone, diphenyl disulfite, methyl o-benzoylbenzoate, ethyl 4-dimethylaminobenzoate [e.g., Kayacure EPA, available from Nippon Kayaku Co., Ltd.], 2,4-diethylthioxanthone [e.g., Kayacure DETX, available from Nippon Kayaku Co., Ltd.], 2-methyl-1-[4-(methyl)phenyl]-2-morpholino-propanone-1 [e.g., Irgacure 907, available from Ciba-Geigy AG], tetra(t-butylperoxycarbonyl) benzophenone, benzil, 2-hydroxy-2-methyl-1-phenyl-propan-1-one, 4,4-bis(diethylamino)benzophenone, and/or 2,2'-bis(2-chlorophenyl)-4,5,4',5'-tetraphenyl-1,2'-biimidazole [e.g., B-CIM, available from Hodagaya Chemical Co., Ltd.] can be used, and as necessary, a photosensitizer can be also added.

The content (blended amount) of the curing catalyst (D) is preferably from 0.01 to 10 parts by weight, more preferably from 0.02 to 7 parts by weight, and even more preferably from 0.03 to 5 parts by weight, per 100 parts by weight of the curable (polymerizable) compound contained in the curable composition. Use of the curing catalyst (D) within the above range readily increases the curing rate of the curable composition and improves the heat resistance and transparency of the cured product in a well-balanced manner.

The curable composition according to an embodiment of the present invention may contain, in addition to the above, one or two or more additives as necessary. Examples of the additive include polyhydric alcohols, such as ethylene glycol, diethylene glycol, propylene glycol, and glycerin; antifoaming agents, leveling agents, silane coupling agents, surfactants, inorganic fillers, flame retardants, colorants, ion adsorbents, pigments, fluorescents, and release agents.

The curable composition according to an embodiment of the present invention can be prepared by stirring and mixing the components described above in a state where the components are heated as necessary. For the stirring and mixing, a well-known or commonly used stirring and mixing means can be used, for example, including a mixer of various types, such as a dissolver and a homogenizer; a kneader; a roll mill; a bead mill; and a rotation/revolution stirring apparatus. In addition, after the stirring and mixing, the mixture may be defoamed under vacuum.

The viscosity of the curable composition according to an embodiment of the present invention at 25° C. is, for example, from 100 to 50000 mPa·s, preferably from 200 to 45000 mPa·s, and particularly preferably from 300 to 40000 mPa·s. Controlling the viscosity at 25° C. to the above range readily improves workability during casting or coating and to be less likely to cause a fault originating from a casting defect or a coating defect in the cured product.

The curable composition according to an embodiment of the present invention at least contains 3,4-epoxycyclohexylmethyl methacrylate having both the cationically polymerizable group and the radically polymerizable group. Therefore, curing of the curable composition according to an embodiment of the present invention can be performed by cationic polymerization, radical polymerization, or a combination of these. When cationic polymerization and radical polymerization are combined, the radical polymerization may be performed first and then the cationic polymerization may be performed, the cationic polymerization may be performed first and then the radical polymerization may be performed, or the cationic polymerization and the radical polymerization may be performed simultaneously.

The curable composition according to an embodiment of the present invention has quick curability. For example, when cationic polymerization (curing) is performed by using a curing agent, the curing time (gel time) at 120° C. is, for example, 2500 seconds or less, and preferably 2400 seconds or less. Furthermore, when cationic polymerization (curing) is performed by using a curing catalyst (thermal cationic polymerization initiator), the curing time (gel time) at 80° C. is, for example, 2000 seconds or less. Furthermore, when cationic polymerization (curing) and radical polymerization are performed simultaneously by using a combination of a thermal cationic polymerization initiator and a thermal radical polymerization initiator as curing catalysts, the curing time (gel time) at 80° C. is, for example, 900 seconds or less.

The heating temperature (curing temperature) at the time of curing of the curable composition according to an embodiment of the present invention is, for example, from 60 to 200° C., and preferably from 80 to 160° C., in the case where a curing agent is used, and is, for example, from 45 to 160° C., and preferably from 60 to 120° C., in the case where a curing catalyst is used. Furthermore, the heating time (curing time) is, for example, from 0.5 to 20 hours, and preferably from 1 to 10 hours. The heating temperature or the heating time below the range listed above would result in insufficient curing. Conversely, the heating temperature or the heating time exceeding the above range would cause decomposition of the resin component. Thus both deviations are not preferred. Although the curing conditions depend on various conditions, the curing conditions can be appropriately adjusted, for example, by shortening the heating time when the heating temperature is increased, or increasing the heating time when the heating temperature is reduced.

When the curable composition according to an embodiment of the present invention is cured, the curing can be performed in an extremely short time period by irradiating with an active energy ray such as ultraviolet light or electron beam. Examples of the light source used during the ultraviolet light irradiation include a high-pressure mercury-vapor lamp, an ultrahigh-pressure mercury-vapor lamp, a carbon-arc lamp, a xenon lamp, and a metal halide lamp. The irradiation time depends on the type of the light source, the distance between the light source and the substrate, and other conditions, but is at most several tens of seconds and typically several seconds. Typically, an irradiation source with a lamp output of approximately from 80 to 300 W/cm is used. For the electron beam irradiation, an electron beam with energy in a range from 50 to 1000 keV is preferably used to provide an irradiation dose from 2 to 5 Mrad. After the irradiation with the active energy ray, heating (post curing) may be performed as necessary to promote the curing.

[Cured Product]

The cured product according to an embodiment of the present invention is produced by curing the curable composition described above. The cured product according to an embodiment of the present invention includes a cured product obtained by subjecting the curable composition according to an embodiment of the present invention to cationic polymerization, a cured product obtained by subjecting the curable composition according to an embodiment of the present invention to radical polymerization, and a cured product obtained by subjecting the curable composition according to an embodiment of the present invention to cationic polymerization and radical polymerization. The cured product according to an embodiment of the present invention (especially, a cured product obtained by cationic polymerization or a cured product obtained by cationic polymerization and radical polymerization) has excellent transparency and heat resistance.

The cured product has excellent transparency. The light transmittance [thickness: 3 mm] of light at a wavelength of 400 nm is, for example, 70% or greater, preferably 80% or greater, and particularly preferably 90% or greater. The curable composition according to an embodiment of the present invention forms a cured product excellent in transparency and thus, when used as an encapsulant, a die attach paste agent, or the like of an optical semiconductor element in an optical semiconductor device, further readily increase the light intensity emitted from the optical semiconductor device.

The cured product has excellent heat resistance. The glass transition temperature (Tg) of the cured product by cationic polymerization is, for example, 60° C. or higher, and preferably 70° C. or higher. The glass transition temperature (Tg) of the cured product by cationic polymerization and radical polymerization is, for example, 140° C. or higher.

In addition, the cured product is excellent in heat resistance and can maintain high light transmittance also in high temperature environments. For example, a sustenance ratio (determined by the equation below) of the light transmittance of light at 400 nm after heating the cured product at 120° C. for 300 hours is, for example, 70% or greater, and preferably 80% or greater.

Sustenance ratio of light transmittance=(light transmittance of cured product after heating)/(light transmittance of cured product before heating)×100

The curable resin composition according to an embodiment of the present invention can be used in various applications, such as, for example, encapsulants, adhesives, coating agents, electrical insulation materials, laminated plates, inks, sealants, resists, composite materials, transparent substrates, transparent sheets, transparent films, optical elements, optical lenses, optical shaping, electronic paper, touch screens, solar cell substrates, optical waveguides, light guiding plates, and holographic memories.

Encapsulant

The encapsulant according to an embodiment of the present invention contains the curable composition described above. The encapsulant according to an embodiment of the present invention can be preferably used in an application of encapsulating an optical semiconductor (optical semiconductor element) in an optical semiconductor device. Use of the encapsulant according to an embodiment of the present invention can encapsulate an optical semiconductor element with a cured product (i.e., an encapsulating material) excellent in transparency and heat resistance.

The proportion of the content of the curable composition in the total amount of the encapsulant according to an embodiment of the present invention is, for example, 50 wt. % or greater, preferably 60 wt. % or greater, and particularly preferably 70 wt. % or greater. The encapsulant according to an embodiment of the present invention may consist of only the curable composition.

Adhesive

The adhesive according to an embodiment of the present invention contains the curable composition. The adhesive according to an embodiment of the present invention can be used in applications to adhere/fix a member or the like to an adherend, in particular, in various applications requiring excellent transparency and heat resistance, such as a die attach paste agent for adhering and fixing an optical semiconductor element to a metal electrode in an optical semiconductor device; a lens adhesive for fixing a lens of a camera or the like to an adherend or bonding lenses together; an optical film adhesive for fixing an optical film (e.g., such as a polarizer, a polarizer protective film, or a retardation films) to an adherend, bonding optical films together, or bonding an optical film with another film.

The adhesive according to an embodiment of the present invention can be preferably used particularly as a die attach paste agent (or a die bond agent). Use of the adhesive according to an embodiment of the present invention as a die attach paste agent provides an optical semiconductor device in which an optical semiconductor element is adhered to an electrode with a cured product excellent in transparency and heat resistance.

The proportion of the content of the curable composition in the total amount of the adhesive according to an embodiment of the present invention is, for example, 50 wt. % or greater, preferably 60 wt. % or greater, and particularly preferably 70 wt. % or greater. The adhesive according to an embodiment of the present invention may consist of only the curable composition.

Coating Agent

The coating agent according to an embodiment of the present invention contains the curable composition. The coating agent according to an embodiment of the present invention can be used particularly in various applications requiring excellent transparency and heat resistance.

The proportion of the content of the curable composition relative to the total amount of the coating agent according to an embodiment of the present invention is, for example, 5 wt. % or greater, preferably 30 wt. % or greater, more preferably 60 wt. % or greater, and particularly preferably 70 wt. % or greater. The coating agent according to an embodiment of the present invention may consist of only the curable composition. Furthermore, the coating agent according to an embodiment of the present invention may also contain a solvent.

Optical Member

An optical member according to an embodiment of the present invention contains the cured product of the curable composition described above. Examples of the optical member includes an optical semiconductor device in which an optical semiconductor element is encapsulated with the cured product of the curable composition described above; an optical semiconductor device in which an optical semiconductor element is adhered to an electrode with the cured product of the curable composition described above; and an optical semiconductor device in which an optical semiconductor element is adhered to an electrode with the cured product of the curable composition described above, and the optical semiconductor element is encapsulated with the cured product of the curable composition described above. The optical member according to an embodiment of the present invention has a configuration in which an optical semiconductor element is encapsulated and adhered with the cured product of the curable composition described above and thus is excellent in heat resistance and has high light extraction efficiency.

The optical member according to an embodiment of the present invention is excellent in heat resistance and can maintain high light transmittance also in high temperature environments. For example, a sustenance ratio (determined by the equation below) of the light transmittance after heating the optical member at 120° C. for 300 hours is, for example, 70% or greater and preferably 75% or greater.

Sustenance ratio of light transmittance=(light transmittance of optical member after heating)/(light transmittance of optical member before heating)×100

EXAMPLES

Hereinafter, the present invention will be described more specifically with reference to examples, but the present invention is not limited by these examples. Note that, unless otherwise noted, "%" representing a concentration means wt. %, and "ppm" representing a concentration means wt. ppm.

Example 1

Epoxidation

In a reactor made of SUS316 having an internal volume of 20 L equipped with a stirrer and a cooling jacket, 3000 g of cyclohexenylmethyl methacrylate (hereinafter, also referred to as CHMA), 11000 g of ethyl acetate, 1.2 g of hydroquinone monomethyl ether, and 9.0 g of sodium tripolyphosphate were added, and a gas mixture of oxygen/nitrogen (10/90 vol. %) was blown into the reactor through an insertion tube at 32 N L/hr. Then, the reaction temperature was maintained at 40° C., and 5166 g of 30% peracetic acid solution was charged over 3 hours by using a metering pump. After completion of the charging, aging was performed for 5 hours, and then the reaction was terminated. By this, 19167 g of a crude reaction solution containing 3,4-epoxycyclohexylmethyl methacrylate (hereinafter, abbreviated as "METHB") was obtained.

Water Washing

Simultaneously, the crude reaction solution containing METHB was charged at a rate of 2108 g/min through a light liquid inlet into a centrifugal extractor in which a rotor having an rotor outer diameter of 46 cm and a rotor internal diameter of 25 mm at a rotation of 4000, and water was charged at a rate of 3590 g/min through a heavy liquid inlet. Thereby, a light liquid was obtained at a rate of 1664 g/min through a light liquid outlet, and a heavy liquid was obtained at a rate of 4034 g/min through a heavy liquid outlet. Simultaneously, the obtained light liquid was charged at a rate of 2108 g/min into the same centrifugal extractor, and water was charged at a rate of 3590 g/min through a heavy liquid inlet. Thereby, a light liquid was obtained at a rate of 1877 g/min through a light liquid outlet, and a heavy liquid was obtained at a rate of 3821 g/min through a heavy liquid outlet. The acetic acid concentration in the light liquid was 400 ppm, and the peracetic acid concentration in the light liquid was 150 ppm.

Alkali Neutralization Treatment

In a treatment tank made of SUS 316 having an internal volume of 15 L equipped with a stirrer and a cooling jacket, 3000 g of the light liquid obtained as described above was charged, and 3000 g of 1% NaOH aqueous solution was charged thereto and agitated for 1 hour while the temperature was maintained at 10° C. The remained peracetic acid concentration in the obtained crude liquid was 100 ppm or less.

Solvent Removal

Then, to 2790 g of this light liquid, 0.16 g of hydroquinone monomethyl ether was added, and solvent removal of a first stage was performed by a Smith type thin film evaporator made of SUS. The operating condition was at a heating temperature of 60° C. and a pressure of 150 mmHg, and a gas mixture of oxygen/nitrogen was blown through a column bottom liquid discharging line at 32 L/hr. This column bottom liquid was subjected to solvent removal of the second stage under the condition of a heating temperature of 60° C. and a pressure of 40 mmHg, and a gas mixture of oxygen/nitrogen (10/90 vol. %) was blown through a column bottom liquid discharging line at 32 N L/hr. The obtained column bottom liquid was 538 g. Furthermore, when the composition of the column bottom liquid was determined by gas chromatography analysis, METHB was 96.4%. As a result of performing heptane test (HT), the polymer content was 0.01%.

Removal of Low-Boiling Fraction

To the METHB (purity: 96.4%) obtained by the method described above, 0.03% of a polymerization inhibitor (N-nitroso-N,N-diphenylamine) was added. This was continuously fed to the tenth tray counted from the bottom of the perforated plate tower (tower diameter 50 mm) having the actual number of trays of 20 (distillation column for removal of low-boiling fractions) at a flow rate of 100 parts by weight/hr, and removal of low-boiling fractions by distillation was performed under the condition of a column top pressure of 0.1 mmHg, a column top temperature of 80° C., a column bottom temperature of 100° C., a heating temperature of 120° C., and a reflux ratio of 3. The flow rate of the column bottom liquid was 90 parts by weight/hr, and the flow rate of the column top distillate was 10 parts by weight/hr.

Removal of High-Boiling Fraction

The column bottom liquid obtained in the removal of low-boiling fractions was continuously fed to the tenth tray counted from the bottom of the perforated plate tower (tower diameter 50 mm) having the actual number of trays of 20 (distillation column for removal of high-boiling fractions) at a flow rate of 100 parts by weight/hr, and removal of high-boiling fractions by distillation was performed under the condition of a column top pressure of 0.1 mmHg, a column top temperature of 80° C., a column bottom temperature of 110° C., a heating temperature of 130° C., and a reflux ratio of 3. The flow rate of the column bottom liquid was 10 parts by weight/hr, and the flow rate of the column top distillate was 90 parts by weight/hr. The column top distillate was collected and obtained as an alicyclic epoxy compound product 1.

Example 2

An alicyclic epoxy compound product 2 was obtained in the same manner as in Example 1 except for changing the reflux ratio of the distillation column for removal of low-boiling fractions to 1 and the reflux ratio of the distillation column for removal of high-boiling fractions to 1.

Example 3

An alicyclic epoxy compound product 3 was obtained in the same manner as in Example 1 except for charging the column bottom liquid of the solvent removal to the fifth tray counted from the bottom in a perforated plate tower (tower diameter 50 mm) having the actual number of trays of 10 (distillation column for removal of low-boiling fractions) and charging the bottom liquid of the distillation column for removal of low-boiling fractions to the fifth tray counted from the bottom in a perforated plate tower (tower diameter 50 mm) having the actual number of trays of 10 (distillation column for removal of high-boiling fractions).

Comparative Example 1

An alicyclic epoxy compound product 4 was obtained in the same manner as in Example 1 except for charging the column bottom liquid of the solvent removal to the second tray counted from the bottom in a perforated plate tower (tower diameter 50 mm) having the actual number of trays of 5 (distillation column for removal of low-boiling fractions) and charging the bottom liquid of the distillation column for removal of low-boiling fractions to the second tray counted from the bottom in a perforated plate tower (tower diameter 50 mm) having the actual number of trays of 5 (distillation column for removal of high-boiling fractions).

Comparative Example 2

An alicyclic epoxy compound product 5 was obtained in the same manner as in Example 1 except for charging the column bottom liquid of the solvent removal to the fifth tray counted from the bottom in a perforated plate tower (tower diameter 50 mm) having the actual number of trays of 10 (distillation column for removal of low-boiling fractions) and performing removal of low-boiling fractions by distillation under the condition of a column top temperature of 110° C., a column bottom temperature of 140° C., and a heating temperature of 160° C., and charging the bottom liquid of the distillation column for removal of low-boiling fractions to the fifth tray counted from the bottom in a perforated plate tower (tower diameter 50 mm) having the actual number of trays of 10 (distillation column for removal of high-boiling fractions) and performing removal of high-boiling fractions by distillation in the condition of a column top temperature of 110° C., a column bottom temperature of 150° C., and a heating temperature of 170° C.

Evaluation of Alicyclic Epoxy Compound Product (1) Purity and Impurity Content

For each of the alicyclic epoxy compound products obtained in Examples and Comparative Examples, the purity of 3,4-epoxycyclohexylmethyl methacrylate [compound represented by Formula (i)], the content of each of the compound represented by Formula (a) [which is the compound (a)], the compound represented by Formula (b) [which is the compound (b)], the compound represented by Formula (c) [which is the compound (c)], and the compound represented by Formula (d) [which is the compound (d)] were measured by using a gas chromatograph under the following condition and calculated based on area %.

Measurement Conditions
Measurement instrument: trade name "GC-2014", available from Shimadzu Corporation
Column filler: (15% PEG-20M) Uniport HPS
Column Size: 2.1 m length×3.2 mmφ internal diameter
Column temperature: the temperature was increased from 100° C. at 10° C./min to 210° C. and maintained for 29 min
Detector: TCD (2) Degree of Coloration For each of the alicyclic epoxy compound product obtained in Examples and Comparative Examples, a degree of coloration was evaluated by determining a Hazen color number (APHA).

(3) Storage Stability

The Hazen color number (APHA) after each of the alicyclic epoxy compound products obtained in Examples and Comparative Examples was stored at 30° C. for 1 month was measured, then the proportion of increase of the Hazen color number (APHA) (Hazen color number after 1 month of storage/Hazen color number immediately after production) was determined. The storage stability of each of the alicyclic epoxy compound products was evaluated based on the following criteria.
Good: less than 2 times
Poor: 2 times or greater The evaluation results of the alicyclic epoxy compound products obtained in Examples and Comparative Examples are shown in Table 1.

(1) Glass Transition Temperature (Tg) of Cured Product

The glass transition temperature of the cured product was determined under the conditions below.
Measurement Conditions
Sample: 4 mm in length×5 mm in width×10 mm in thickness
Measurement apparatus: thermomechanical measurement apparatus (TMA), "TMA/SS6000 (trade name)", available from Seiko Instruments Co., Ltd.
Measurement mode: compression (needle penetration), constant load measurement
Measurement temperature: from 25° C. to 300° C.
Rate of temperature increase: 5° C./min (2) Transparency of Cured Product The light transmittance (thickness direction; % T) of light at a wavelength of 400 nm of the cured product (thickness: 3 mm) was measured using a spectrophotometer ("UV-2400 (trade name)", available from Shimadzu Corporation).

(3) Overall Judgment

For Examples 4 to 6 and Comparative Examples 3 and 4
Good: Tg is 70° C. or higher and transparency is 70% or greater
Poor: Tg is lower than 70° C. or transparency is less than 70%
For Examples 7 to 9 and Comparative Examples 5 and 6
Good: Tg is 60° C. or higher and transparency is 70% or greater

TABLE 1

| | Alicyclic epoxy compound product No. | Purity of compound represented by Formula (1) (wt. %) | Content of compound (a) (wt. %) | Content of compound (b) (wt. %) | Total content of compounds (a), (b) (wt. %) | Content of compound (c) (wt. %) | Total content of compounds (a), (b), (c) (wt. %) | Content of compound (d) (wt. %) | Total content of compounds (a), (b), (c), (d) (wt. %) | APHA | Storage stability |
|---|---|---|---|---|---|---|---|---|---|---|---|
| Example 1 | 1 | 99.96 | 0.01 | 0.01 | 0.02 | 0.01 | 0.03 | 0.01 | 0.04 | 5 | Good |
| Example 2 | 2 | 99.90 | 0.01 | 0.04 | 0.05 | 0.02 | 0.07 | 0.03 | 0.10 | 7 | Good |
| Example 3 | 3 | 98.20 | 0.24 | 0.77 | 1.01 | 0.28 | 1.29 | 0.51 | 1.80 | 15 | Good |
| Comparative Example 1 | 4 | 97.50 | 0.34 | 1.07 | 1.41 | 0.38 | 1.79 | 0.71 | 2.50 | 56 | Poor |
| Comparative Example 2 | 5 | 96.60 | 0.47 | 1.45 | 1.92 | 0.51 | 2.43 | 0.97 | 3.40 | 60 | Poor |

Examples 4 to 12 and Comparative Examples 3 to 8

The components were blended according to formulations (unit: part by weight) shown in Tables 2 to 4 below, stirred using a rotation/revolution stirring apparatus (trade name "THINKY MIXER AR-250", available from Thinky Corporation), and further defoamed, and thus a curable composition was obtained.

Evaluation of Cured Product of Curable Composition

Each of the curable compositions was filled into a mold and heated in a resin curing oven at a predetermined temperature for a predetermined time period to produce a cured product, and a glass transition temperature and transparency of the resulting cured product were evaluated by the following methods. Note that the curing condition at the time of curing is as described below.
Examples 4 to 6 and Comparative Examples 3 and 4: 120° C.×5 hours
Examples 7 to 9 and Comparative Examples 5 and 6: 80° C.×2 hours and then 140° C.×2 hours
Examples 10 to 12 and Comparative Examples 7 and 8: 80° C.×2 hours and then 110° C.×3 hours Poor: Tg is lower than 60° C. or transparency is less than 70%
For Examples 10 to 12 and Comparative Examples 7 and 8
Good: Tg is 140° C. or higher and transparency is 90% or greater
Poor: Tg is lower than 140° C. or transparency is less than 90%

Evaluation of Optical Semiconductor Device

Each of the curable compositions was cast into a lead frame (InGaN element, 3.5 mm×2.8 mm) of an optical semiconductor, then the curable composition was heated in an oven at 120° C. for 5 hours. Thus, an optical semiconductor device in which an optical semiconductor element was encapsulated with a cured product of the curable composition was obtained (see FIG. 1). Brightness and heat resistance of the resulting optical semiconductor devices were evaluated.

(1) Evaluation of Brightness

The brightness (lumen: lm) of the optical semiconductor device was measured by measuring total luminous flux of the optical semiconductor device using a total luminous flux measurement apparatus ("Multispectral Radiation Measurement System OL771 (trade name)", available from Optronic Laboratories).

(2) Evaluation of Heat Resistance

The heat resistance of the optical semiconductor device was evaluated by subjecting the optical semiconductor device to a heat treatment (aging) at 120° C. for 300 hours, calculating a retention ratio of the light transmittance from the equation below. This was used as an index of the heat resistance.

Retention ratio (%) of light transmittance=(light transmittance of optical semiconductor device after heat treatment/light transmittance of optical semiconductor device before heat treatment)×100

(3) Overall Judgment

For Examples 4 to 6 and Comparative Examples 3 and 4
Good: Brightness is 0.60 lm or greater and heat resistance is 70% or greater
Poor: Brightness is less than 0.60 lm or heat resistance is less than 70%
For Examples 7 to 9 and Comparative Examples 5 and 6
Good: Brightness is 0.60 lm or greater and heat resistance is 70% or greater
Poor: Brightness is less than 0.60 lm or heat resistance is less than 70%
For Examples 10 to 12 and Comparative Examples 7 and 8
Good: Brightness is 0.70 lm or greater and heat resistance is 80% or greater
Poor: Brightness is less than 0.70 lm or heat resistance is less than 80%

Evaluation of Coating Agent

Each of the curable compositions was used as a coating agent. The reactivity was evaluated by the following method.

(1) Reactivity (Gel Time)

Reactivity of each of the curable compositions (coating agents) was measured using a gel time measurement apparatus (trade name "No. 153 Gel Time Tester (Magnet Type)", available from Yasuda Seiki Seisaku-sho, Ltd.). Note that, in Examples 4 to 6 and Comparative Examples 3 and 4, reactivity (curability; gel time) at the time of heating at 120° C. was evaluated, and in Examples 7 to 12 and Comparative Examples 5 to 8, reactivity (curability; gel time) at the time of heating at 80° C. was evaluated.

(2) Overall Judgment

For Examples 4 to 6 and Comparative Examples 3 and 4
Good: Gel time at 120° C. is 2400 seconds or shorter
Poor: Gel time at 120° C. is longer than 2400 seconds
For Examples 7 to 9 and Comparative Examples 5 and 6
Good: Gel time at 80° C. is 2000 seconds or shorter
Poor: Gel time at 80° C. is longer than 2000 seconds
For Examples 10 to 12 and Comparative Examples 7 and 8
Good: Gel time at 80° C. is 900 seconds or shorter
Poor: Gel time at 80° C. is longer than 900 seconds Evaluation results of the cured product of each of the curable compositions, optical semiconductor device obtained by using each of the curable compositions, and coating agent using each of the curable compositions are shown in Tables 2 to 4.

TABLE 2

| | | Example 4 | Example 5 | Example 6 | Comparative Example 3 | Comparative Example 4 |
|---|---|---|---|---|---|---|
| Curable composition | Alicyclic epoxy compound product 1 | 100 | — | — | — | — |
| | Alicyclic epoxy compound product 2 | — | 100 | — | — | — |
| | Alicyclic epoxy compound product 3 | — | — | 100 | — | — |
| | Alicyclic epoxy compound product 4 | — | — | — | 100 | — |
| | Alicyclic epoxy compound product 5 | — | — | — | — | 100 |
| | MH-700 | 100 | 100 | 100 | 100 | 100 |
| | 18X | 0.5 | 0.5 | 0.5 | 0.5 | 0.5 |
| | Ethylene glycol | 1 | 1 | 1 | 1 | 1 |
| Evaluation of cured product | Tg (° C.) | 78 | 75 | 73 | 69 | 66 |
| | Transparency (% T) | 75 | 74 | 72 | 69 | 68 |
| | Overall judgment | Good | Good | Good | Poor | Poor |
| Optical material (optical semiconductor device) evaluation | Transparency [lm] | 0.69 | 0.68 | 0.65 | 0.59 | 0.57 |
| | Heat resistance (%) | 76 | 74 | 72 | 69 | 67 |
| | Overall judgment | Good | Good | Good | Poor | Poor |
| Coating agent evaluation | Reactivity [sec] | 2240 | 2280 | 2400 | 2540 | 2630 |
| | Overall judgment | Good | Good | Good | Poor | Poor |

TABLE 3

| | | Example 7 | Example 8 | Example 9 | Comparative Example 5 | Comparative Example 6 |
|---|---|---|---|---|---|---|
| Curable composition | Alicyclic epoxy compound product 1 | 100 | — | — | — | — |
| | Alicyclic epoxy compound product 2 | — | 100 | — | — | — |
| | Alicyclic epoxy compound product 3 | — | — | 100 | — | — |

TABLE 3-continued

| | | Example 7 | Example 8 | Example 9 | Comparative Example 5 | Comparative Example 6 |
|---|---|---|---|---|---|---|
| | Alicyclic epoxy compound product 4 | — | — | — | 100 | — |
| | Alicyclic epoxy compound product 5 | — | — | — | — | 100 |
| | SI-100L | 0.5 | 0.5 | 0.5 | 0.5 | 0.5 |
| Evaluation of cured product | Tg (° C.) | 67 | 65 | 63 | 58 | 56 |
| | Transparency (% T) | 73 | 71 | 70 | 69 | 68 |
| | Overall judgment | Good | Good | Good | Poor | Poor |
| Optical material (optical semiconductor device) evaluation | Transparency [lm] | 0.66 | 0.63 | 0.62 | 0.57 | 0.54 |
| | Heat resistance (%) | 74 | 72 | 70 | 68 | 65 |
| | Overall judgment | Good | Good | Good | Poor | Poor |
| Coating agent evaluation | Reactivity [sec] | 1840 | 1900 | 1930 | 2020 | 2060 |
| | Overall judgment | Good | Good | Good | Poor | Poor |

TABLE 4

| | | Example 10 | Example 11 | Example 12 | Comparative Example 7 | Comparative Example 8 |
|---|---|---|---|---|---|---|
| Curable composition | Alicyclic epoxy compound product 1 | 100 | — | — | — | — |
| | Alicyclic epoxy compound product 2 | — | 100 | — | — | — |
| | Alicyclic epoxy compound product 3 | — | — | 100 | — | — |
| | Alicyclic epoxy compound product 4 | — | — | — | 100 | — |
| | Alicyclic epoxy compound product 5 | — | — | — | — | 100 |
| | Perbutyl O | 0.6 | 0.6 | 0.6 | 0.6 | 0.6 |
| | SI-100L | 0.5 | 0.5 | 0.5 | 0.5 | 0.5 |
| Evaluation of cured product | Tg (° C.) | 146 | 144 | 142 | 139 | 138 |
| | Transparency (% T) | 92 | 91 | 90 | 89 | 88 |
| | Overall judgment | Good | Good | Good | Poor | Poor |
| Optical material (optical semiconductor device) evaluation | Transparency [lm] | 0.78 | 0.76 | 0.71 | 0.68 | 0.66 |
| | Heat resistance (%) | 85 | 83 | 81 | 79 | 78 |
| | Overall judgment | Good | Good | Good | Poor | Poor |
| Coating agent evaluation | Reactivity [sec] | 810 | 830 | 880 | 910 | 940 |
| | Overall judgment | Good | Good | Good | Poor | Poor |

Abbreviations in the tables are described below.

MH700: curing agent, 4-methylhexahydrophthalic anhydride/hexahydrophthalic anhydride=70/30, "RIKACID MH-700 (trade name)", available from New Japan Chemical Co., Ltd.

18X: curing accelerator, special amine, "U-CAT 18X (trade name)", available from San-Apro Ltd.

SI-100L: curing catalyst (thermal cationic polymerization initiator), "SAN-AID SI-100L (trade name)", available from Sanshin Chemical Industry Co., Ltd.

Perbutyl O: curing catalyst (radical polymerization initiator)

To summarize the above, configurations and variations according to an embodiment of the present invention will be described below.

[1] An alicyclic epoxy compound product having a purity of 3,4-epoxycyclohexylmethyl methacrylate of 98.0 wt. % or greater and a total content of a compound represented by Formula (a) below and a compound represented by Formula (b) below of 1.3 wt. % or less.

[Chem. 11]

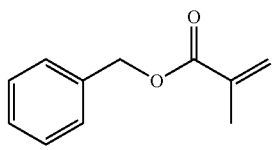
(a)

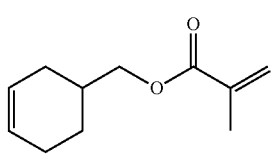
(b)

[2] The alicyclic epoxy compound product according to [1] above, where a total content of the compound represented by Formula (a) above, the compound represented by Formula (b) above, and a compound represented by Formula (c) below is 1.6 wt. % or less.

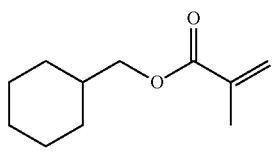

(c)

[3] The alicyclic epoxy compound product according to [1] or [2] above, where a total content of the compound represented by Formula (a) above, the compound represented by Formula (b) above, the compound represented by Formula (c) above, and a compound represented by Formula (d) below is 2.0 wt. % or less.

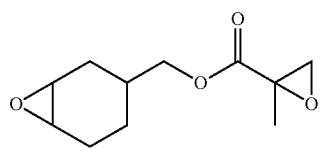

(d)

[4] The alicyclic epoxy compound product according to any one of [1] to [3] above, where a content of the compound represented by Formula (a) above is 0.3 wt. % or less.

[5] The alicyclic epoxy compound product according to any one of [1] to [4] above, where a content of the compound represented by Formula (b) above is 1.0 wt. % or less.

[6] The alicyclic epoxy compound product according to any one of [1] to [5] above, where a content of the compound represented by Formula (c) above is 0.3 wt. % or less.

[7] The alicyclic epoxy compound product according to any one of [1] to [6] above, where a content of the compound represented by Formula (d) above is 0.6 wt. % or less.

[8] The alicyclic epoxy compound product according to any one of [1] to [7] above, where a Hazen color number is 25 or less.

[9] The alicyclic epoxy compound product according to any one of [1] to [8] above, where a percentage of increase of a Hazen color number after the alicyclic epoxy compound product is stored at 30° C. for 1 month is less than 20%.

[10] A curable composition containing the alicyclic epoxy compound product according to any one of [1] to [9] above.

[11] The curable composition according to [10] above, further containing a curing agent and a curing accelerator.

[12] The curable composition according to [10] above, further containing a curing catalyst.

[13] A cured product of the curable composition according to any one of [10] to [12] above.

[14] An encapsulant containing the curable composition according to any one of [10] to [12] above.

[15] An adhesive agent containing the curable composition according to any one of [10] to [12] above.

[16] A coating agent containing the curable composition according to any one of [10] to [12] above.

[17] An optical member including a member formed from the cured product according to [13] above.

[18] A method of producing an alicyclic epoxy compound product including epoxidation of obtaining a reaction product by epoxidizing 3-cyclohexenylmethyl methacrylate with an organic peracid, and including, in no particular order, removal of low-boiling fractions of removing low-boiling fractions contained in the reaction product by distillation, and removal of high-boiling fractions of removing high-boiling fractions contained in the reaction product by distillation.

[19] The method of producing an alicyclic epoxy compound product according to [18] above, further including at least one selected from the group consisting of water washing of washing the reaction product with water, alkali neutralization treatment of neutralizing the reaction product with an alkali, alkali solution washing of washing the reaction product with an alkali aqueous solution, and solvent removal of removing a solvent contained in the reaction product.

INDUSTRIAL APPLICABILITY

Because the alicyclic epoxy compound product according to an embodiment of the present invention contains high-purity 3,4-epoxycyclohexylmethyl methacrylate and has a low content of particular impurities, by curing a curable composition containing this alicyclic epoxy compound product, a cured product having excellent transparency and heat resistance can be obtained. The curable resin composition according to an embodiment of the present invention can be used in various applications, such as, for example, encapsulants, adhesives, coating agents, electrical insulation materials, laminated plates, inks, sealants, resists, composite materials, transparent substrates, transparent sheets, transparent films, optical elements, optical lenses, optical shaping, electronic paper, touch screens, solar cell substrates, optical waveguides, light guiding plates, and holographic memories.

REFERENCE SIGNS LIST

1 Reflector
2 Encapsulating material of optical semiconductor element
3 Bonding wire
4 Optical semiconductor element
5 Die bonding material
6 Metal wiring

The invention claimed is:

1. An alicyclic epoxy compound product having a purity of 3,4-epoxycyclohexylmethyl methacrylate of 99.5 wt. % or greater and a total content of a compound represented by Formula (a) and a compound represented by Formula (b) of 0.09 wt. % or less, wherein a Hazen color number is 7 or less;

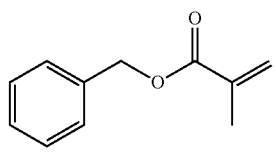

(a)

-continued

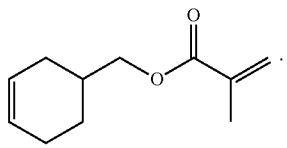
(b)

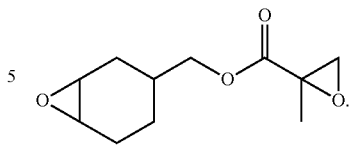
(d)

2. The alicyclic epoxy compound product according to claim 1, wherein a total content of the compound represented by Formula (a), the compound represented by Formula (b), and a compound represented by Formula (c) below is 0.2 wt. % or less;

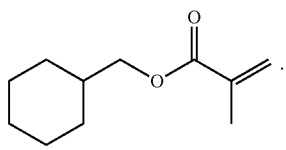
(c)

3. The alicyclic epoxy compound product according to claim 2, wherein a total content of the compound represented by Formula (a), the compound represented by Formula (b), the compound represented by Formula (c), and a compound represented by Formula (d) is 0.2 wt. % or less;

4. A curable composition containing the alicyclic epoxy compound product according to claim 1.

5. The curable composition according to claim 4, further comprising a curing agent and a curing accelerator.

6. The curable composition according to claim 4, further comprising a curing catalyst.

7. A cured product of the curable composition according to claim 4.

8. An optical member comprising a member formed from the cured product according to claim 7.

9. An encapsulant comprising the curable composition according to claim 4.

10. An adhesive agent comprising the curable composition according to claim 4.

11. A coating agent comprising the curable composition according to claim 4.

* * * * *